(12) United States Patent
Chandler et al.

(10) Patent No.: US 10,465,193 B2
(45) Date of Patent: Nov. 5, 2019

(54) MODULATION OF ALTERNATIVE MDM2 SPLICING

(71) Applicant: Research Institute at Nationwide Children's Hospital, Columbia, OH (US)

(72) Inventors: Dawn Suzan Chandler, Bexley, OH (US); Daniel Forrest Comiskey, Jr., Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 15/594,054

(22) Filed: May 12, 2017

(65) Prior Publication Data
US 2017/0355993 A1 Dec. 14, 2017

Related U.S. Application Data

(63) Continuation-in-part of application No. PCT/US2015/060349, filed on Nov. 12, 2015.

(60) Provisional application No. 62/078,603, filed on Nov. 12, 2014.

(51) Int. Cl.
| | |
|---|---|
| C07H 21/04 | (2006.01) |
| C12N 15/113 | (2010.01) |
| A61K 31/7088 | (2006.01) |
| A61K 31/713 | (2006.01) |

(52) U.S. Cl.
CPC ...... *C12N 15/1135* (2013.01); *A61K 31/7088* (2013.01); *A61K 31/713* (2013.01); *C12N 15/113* (2013.01); *C12N 2310/11* (2013.01); *C12N 2310/14* (2013.01); *C12N 2310/315* (2013.01); *C12N 2310/321* (2013.01); *C12N 2320/33* (2013.01)

(58) Field of Classification Search
CPC .................................................. C12N 15/111
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 5,013,556 A | 5/1991 | Woodle et al. | |
| 2003/0203862 A1 | 10/2003 | Miraglia et al. | |
| 2005/0176975 A1 | 8/2005 | Johnson et al. | |

OTHER PUBLICATIONS

Krainer, A.R., et al. The Essential Pre-mRNA Splicing Factor SF2 Influences 5'Splice Site Selection by Activating Proximal Sites. *Cell*, (1990). vol. 62, pp. 35-42.

Li, X., et al. Inactivation of the SR Protein Splicing Factor ASF/SF2 Results in Genomic Instability, *Cell*, (2005), vol. 122, pp. 365-368.

Karni, R., et al., The gene encoding the splicing factor SF2/ASF is a proto-oncogene. *Nat. Struct. Mol. Biol.*, (2007), vol. 14(3), pp. 185-193.

Fang, S., et al. Mdm2 is a RING Finger-dependent Ubiquitin Protein Ligase for Itself and p53, *J Biol. Chem.*, (2000), vol. 275, No. 12, pp. 8945-8951.

Chandler, D.S., et al. Genotoxic Stress Induces Coordinately Regulated Alternative Splicing of the p53 Modulators MDM2 and MDM4. *Cancer Res.* (2006), vol. 66(19), pp. 9502-9508.

Jacob., A.G., et al. Stress-Induced Alternative Splice Forms of MDM2 and MDMX Modulate the p52-Pathway in Distinct Ways, *PLOS One*, (2014), vol. 9, Issue 8, e104444.

Sigalas, I., et al. Alternatively spliced mdm2 transcripts with loss of p53 binding domain sequences: Transforming ability and frequent detection in human cancer. *Nature Medicine*, (1996), vol. 2, No. 8, pp. 912-917.

Yu, Z., et al. Identification of Spliced Variants of the Proto-Oncogene HDM2 in Colorectal Cancer, *Cancer*, (2012), vol. 118, pp. 1110-1118.

Dutertre, M., et al. Cotranscriptiorial exon skipping in the genotoxic stress response. *Nat. Struct. Mol. Biol.*, (2010), vol. 17, No. 11, pp. 1358-1366.

Singh, R.K., et al, Conserved sequences in the final intron of MDM2 are essential for the regulation of alternative splicing of MDM2 in response. *Exp. Cell Res*, (2009), vol. 315, pp. 3419-3422.

Jacob, A.G., et al. The Splicing Factor FUBP1 is Required for the Efficient Splicing of Oncogene MDM2 Pre-mRNA. *J. Biol. Chem.*, (2014), vol. 289, No. 25, pp. 17350-17364.

Werle, M., et al. Chitosan-aprotinin coated liposomes for oral peptide delivery: Development, charaterisation and in vivo evaluation. *Int. J. Pharm.*, (2009), vol. 370, pp. 26-32.

Heitz, F., et al., Twenty years of cell-penetrating peptides; from molecular mechanisms to therapeutics. *Br J Pharm.*, (2009), vol. 157, pp. 195-206.

Jeyaraj, S.C., et al. MDM2 and MDM4 splicing: an integral part of the cancer spliceome. *Front. Biosci.*, (2009), vol. 14, pp. 2647-2656.

Smith, P.J., et al. An increased specificity score matrix for the prediction of SF2/ASF-specific exonic splicing enhancers. *Hum. Mol. Genet.*, (2006), vol. 15, No. 16, pp. 2490-2508.

MacLeod K.F., et al. p53-Dependent and independent expression of p21 during cell growth, differentiation, and DNA damage. *Genes. & Dev.* (1995), vol. 9, pp. 935-944.

Rockx, D.A.P., et al. UV-induced inhibition of transcription involves repression of transcription initiation and phosphorylation of RNA polymerase II, *PNAS*, (2000), vol. 97, No. 19, pp. 10503-10508.

Sun, S., et al. SF2/ASF Autoregulation involves Multiple Layers of Post-transcriptional and Translational Control, *Nat. Struct, Mol. Biol.*, (2010), vol. 17(3), pp. 306-312.

Hori, M., et al. Alternatively spliced MDM2 transcripts in human breast cancer in relation to tumor necrosis and lymph node involvement, *Path. Internati.*, (2000), vol. 50, pp. 786-792.

(Continued)

*Primary Examiner* — Kimberly Chong
(74) *Attorney, Agent, or Firm* — Benesch, Friedlander, Coplan & Aronoff LLP

(57) ABSTRACT

Compositions and methods for treating cancer in a subject in need thereof are described that includes administering a therapeutically effective amount of an oligonucleotide that inhibits the binding of splicing regulator SRSF1 or SRSF2 to MDM2 exon 4 or 11.

11 Claims, 14 Drawing Sheets

Specification includes a Sequence Listing.

(56) References Cited

OTHER PUBLICATIONS

Kraus, A., et al. Expression of Alternatively Spliced mdm2 Transcripts Correlates with Stabilized Wild-Type p53 Protein in Human Glioblastoma Cells. *Int J. Cancer*, (1999), vol. 80, pp. 930-934.

Jacob, A.G., et al. Stress-Induced Isoforms of MDM2 and MDM4 Correlate with High-Grade Disease and an Altered Splicing Network in Pediatric Rhabdomyosarcoma. *Neoplasia*, (2013), vol. 15, No. 9, pp. 1049-1063.

Han, J., et al. SR Proteins Induce Alternative Exon Skipping through Their Activities on the Flanking Constitutive Exons. *Mol. Cell Biol.*, (2011), vol. 31, No. 4, pp. 793-802.

De Miguel, F.J., et al. Identification of Alternative Splicing Events Regulated by the Oncogenic SRSF1 in Lung Cancer. *Cancer Res.*, (2013), vol. 74(4), pp. 1105-1115.

Ghigna, C., et al. Cell Motility is Controlled by SF2/ASF through Alternative Splicing of the Ron Protooncogene. *Mol. Cell*, (2006), vol. 20, pp. 881-890.

Buratti, E., et al. SR protein-mediated inhibition of CFTR exon 9 inclusion: molecular characterization of the intronic splicing silencer. *Nucleic Acids Res.*, (2007), vol. 35, No. 13, pp. 4359-4368.

Ibrahim, E.C., et al. Serine/arginine-rich protein-dependent suppression of exon skipping by exonic splicing enhancers. *PNAS*, (2005), vol. 102, No. 14, pp. 5002-5007.

Shen, M., et al. Activation and repression functions of an SR splicing regulator depend on exonic versus intronic-binding position. *Nucleic Acids Res.*, (2012) vol. 40, No. 1, pp. 428-437.

Goren, A., et al. Comparative Analysis Identifies Exonic Splicing Regulatory Sequences—The Complex Definition of Enhancers and Silencers. *Mol. Cell*, (2006), vol. 22, pp. 769-781.

Wang, J., et al. Distribution of SR protein exonic splicing enhancer motifs in human protein-coding genes. *Nucleic Acids Res.*, (2005), vol. 33, No. 16, pp. 5053-5062.

Holste, D., et al. Strategies for Identifying RNA Splicing Regulatory Motifs and Predicting Alternative Splicing Events. *PLoS Comput. Biol.*, (2008), vol. 4, Issue 1, e21.

Zhong, X.-Y., et al. Regulation of SR protein phosphoryistion and alternative splicing by modulating kinetic interactions of SRPK1 with molecular chaperones. *Genes & Dev.*, (2009), vol. 23, pp. 482-495.

Sinclair, C.S., et al. The 17q23 amplicon and breast cancer. *Breast Cancer Res. Treat*, (2003), vol. 78, pp. 313-322.

Das, S., et al. Oncogenic Splicing Factor SRSF1 is a Critical Transcriptional Target of MYC. *Cell Rep.*, (2012), vol. 1(2), pp. 110-117.

Steinman, H.A., et al. An Alternative Splice Form of Mdm2 Induces p53-independent Cell Growth and Tumorigenesis, *J Biol. Chem.*, (2004). vol. 279, No. 6, pp. 4877-4886.

Fridman, J.S., et al. Tumor Promotion by Mdm2 Splice Variants Unable to Bind p53. *Cancer Res.*, (2003), vol. 63, pp. 5703-5705.

Zheng, T., et al. Spliced MDM2 isoforms promote mutant p53 accumulation and gain-of-function in tumorigenesis. *Nat. Commun.*, (2013), vol. 4, pp. 1-26.

Yoo, B.H., et al. 2'-O-methyl-modified phosphorothiate antisense oligonucleotides have reduced non-specific effects in vitro. *Nucleic Acids Res.*, (2004), vol. 32, No. 6, pp. 2008-2016.

Comiskey, D.F., et al. Splicing factor SRSF1 negatively regulates alternative splicing of MDM2 under damage. *Nucleic Acids Res.*, (2015), vol. 43(8). pp. 4202-4228.

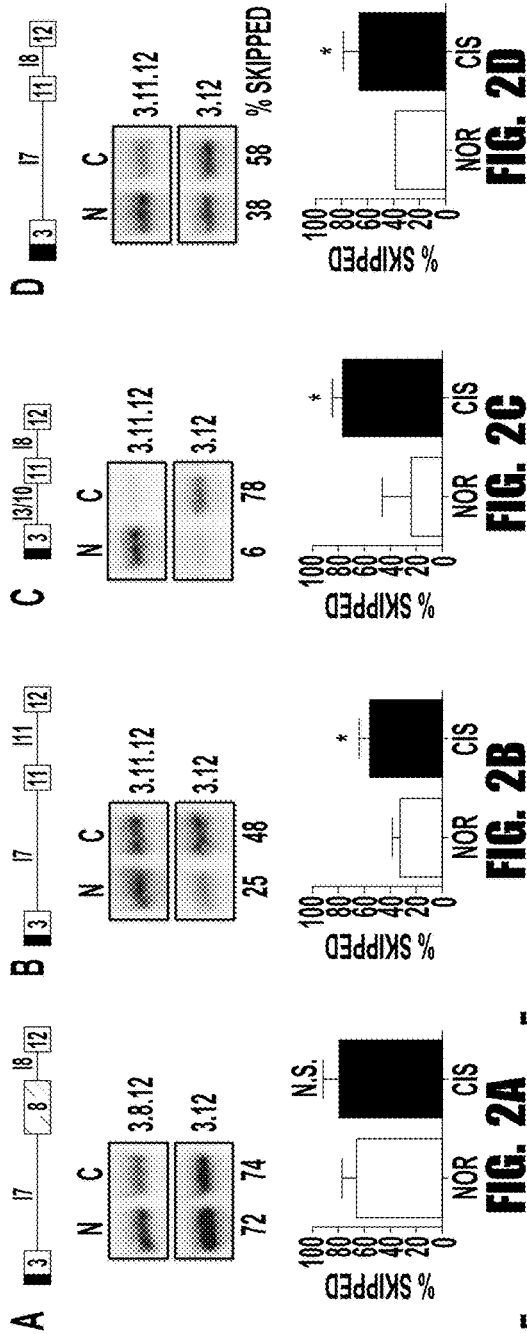
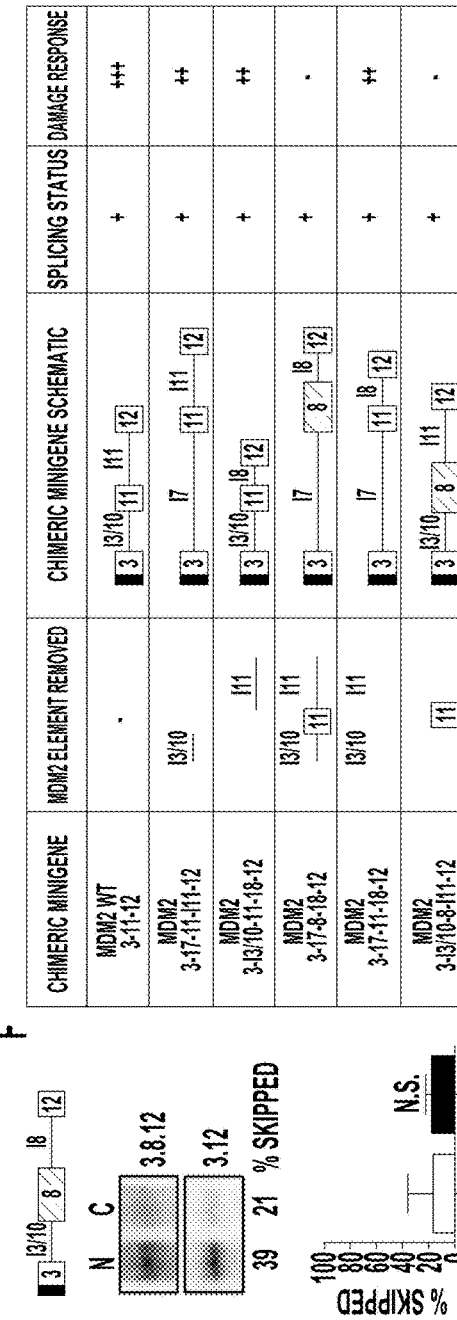

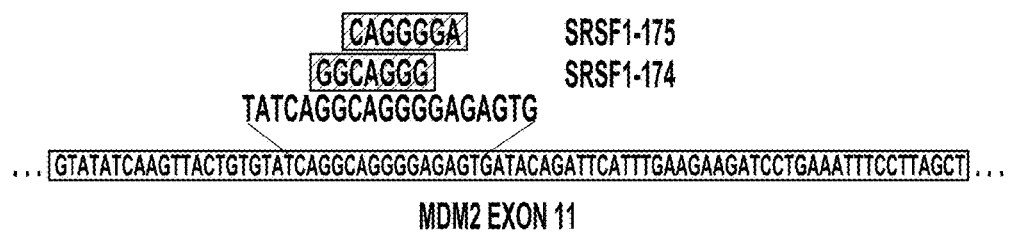
FIG. 6A
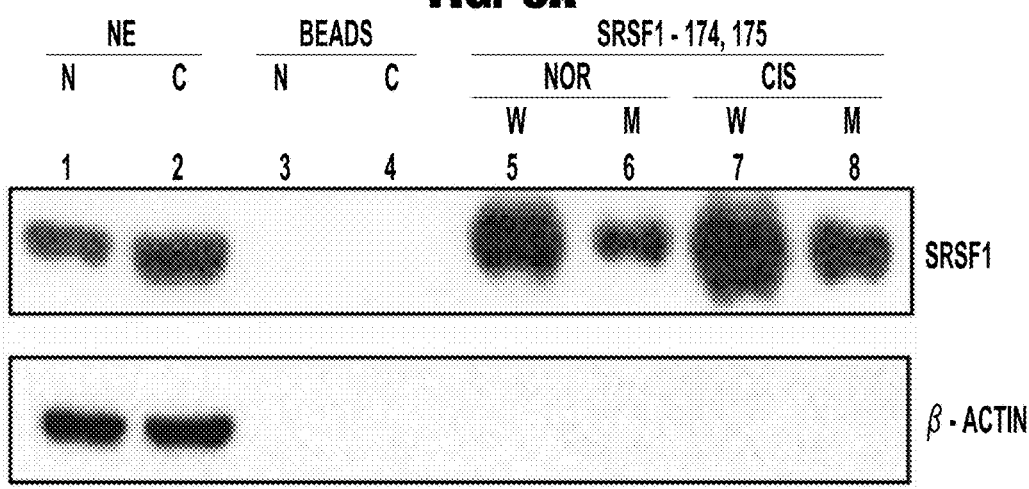
FIG. 6B
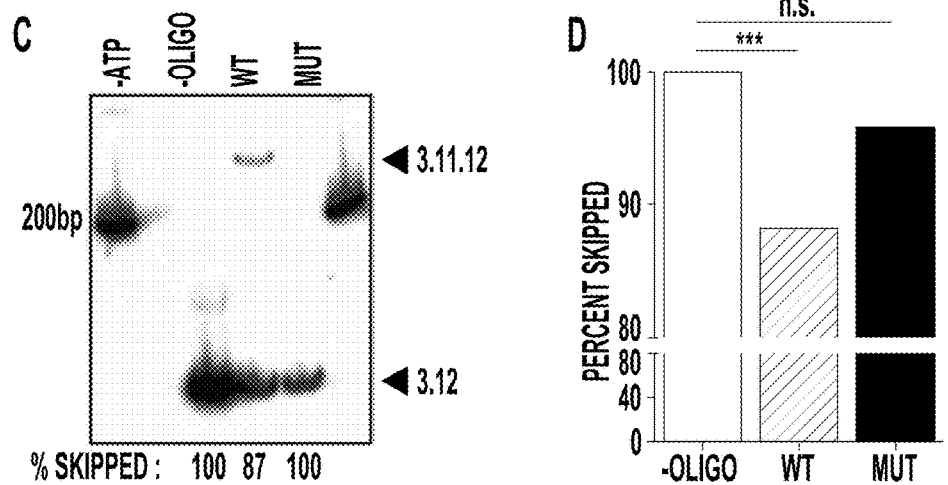
FIG. 6C
FIG. 6D

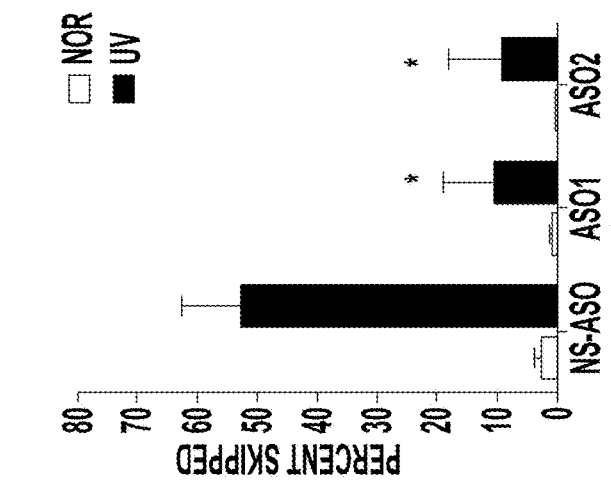
FIG. 7A
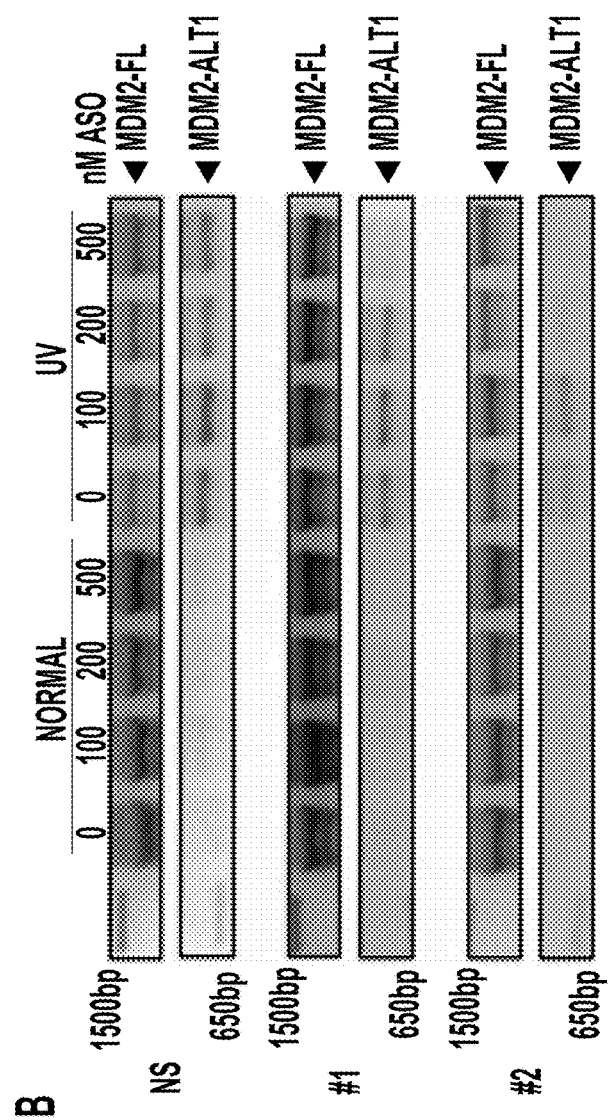
FIG. 7B
FIG. 7C

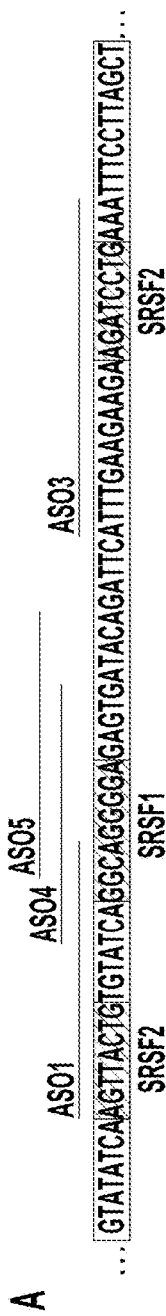
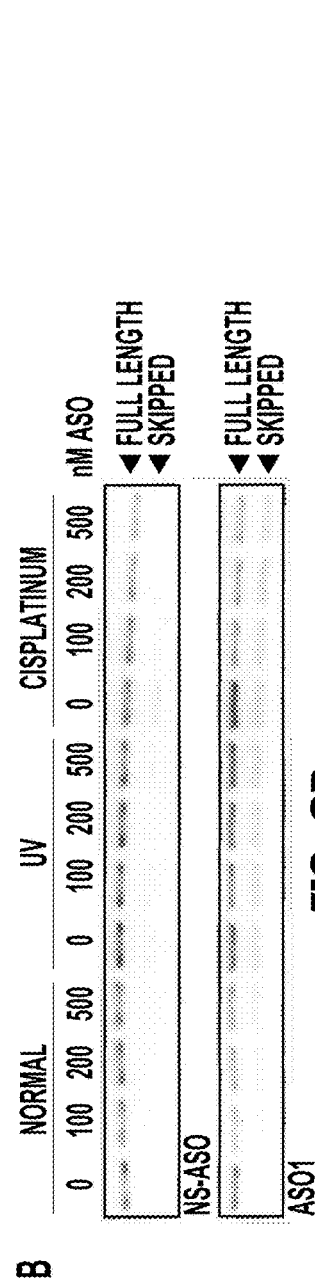
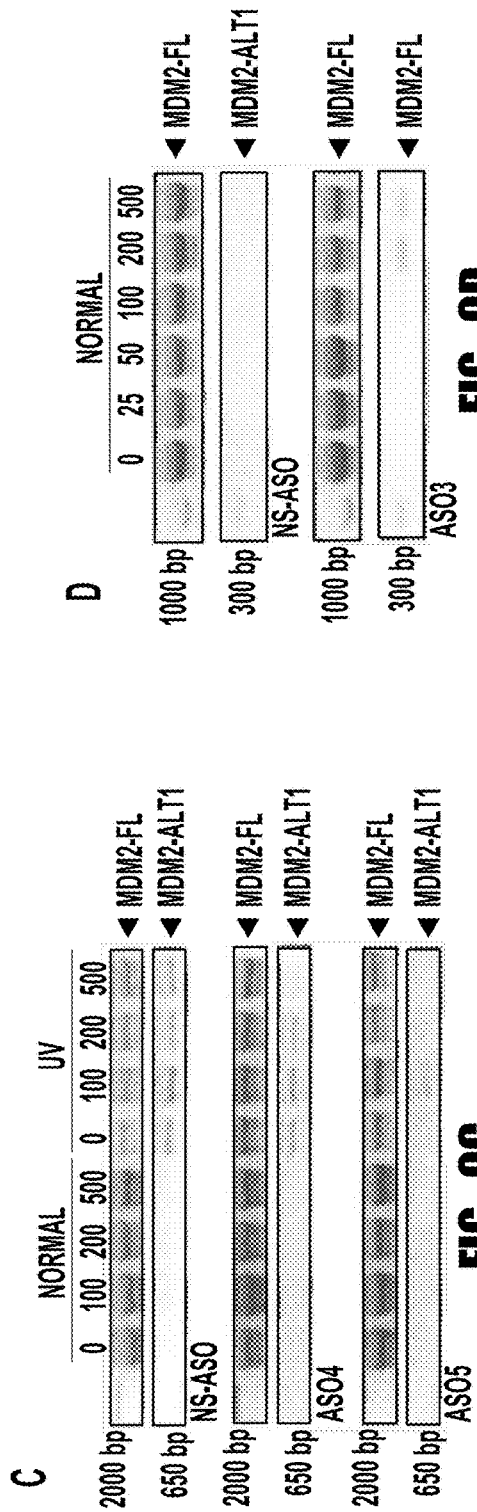
FIG. 9A
FIG. 9B
FIG. 9C
FIG. 9D

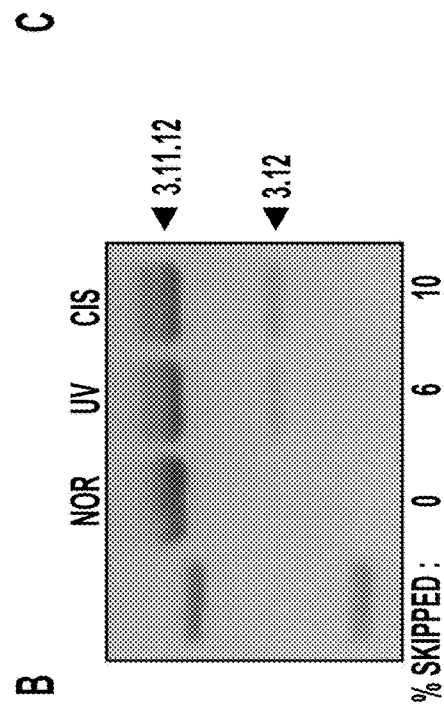

MODULATION OF ALTERNATIVE MDM2 SPLICING

CROSS-REFERENCE TO RELATED APPLICATIONS

This application claims priority to International Patent Application No. PCT/US2015/060349, filed on Nov. 12, 2015, which claims priority to U.S. Provisional Patent Application Ser. No. 62/078,603, filed Nov. 12, 2014, both of which are incorporated herein by reference.

GOVERNMENT FUNDING

This invention was made with Government support under grant number R01CA1335710 awarded by the National Institutes of Health and the National Cancer Institute. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 12, 2015, is named antisense MDM2 NCH-023869 WO ORD_ST25 and is 5,613 bytes in size.

BACKGROUND

Alternative splicing is an important cellular process that contributes to proteome diversity. It is estimated that greater than 95% of all genes undergo alternative splicing. These alternative splicing events are often spatially and temporally regulated and generated in response to external stimuli. In general, the regulation of alternative splicing is achieved through complex interplay between cis-regulatory elements within the pre-mRNA and the trans protein factors that bind them. Trans-binding protein factors belong to two general classes: serine-arginine rich (SR) proteins and heterogenous ribonucleoproteins (hnRNPs), whose canonical roles are to either promote or repress the inclusion of an exon in the nascent pre-mRNA transcript, respectively. The balance in the levels of these factors and their binding to specific sites on the pre-mRNA is key toward influencing the decisions of the spliceosome, thereby enabling splicing regulation. SRSF1, formerly SF2/ASF, is one such member of the serine-arginine rich family of SR proteins. In addition to its role in alternative splicing, SRSF1 is required to mediate canonical splicing events including 5' splice site selection and lariat formation of the major spliceosome. Krainer et al., Cell, 62, 35-42 (1990); Li, X. and Manley, J. L. Cell, 122, 365-378 (2005). SRSF1 is an important proto-oncogene due to its role in the alternative splicing regulation of several cancer-associated genes. Karni, et al., Nat Struct Mol Biol, 14, 185-193 (2007).

Murine Double Minute 2 (MDM2) is an E3 ubiquitin ligase and negative regulator of the tumor suppressor protein p53. Under normal conditions, MDM2 is constitutively spliced to generate a full-length protein, which self-dimerizes and promotes the proteasome-mediated degradation of p53. Fang et al., J Biol Chem, 275, 8945-8951 (2000). However, under stress MDM2 undergoes alternative splicing, generating splice variants that are unable to bind and regulate p53. Chandler et al., Cancer Res, 66, 9502-9508. Subsequently, p53 becomes upregulated and activates downstream targets involved in apoptosis and cell cycle arrest. Jacob et al., PLoS One, 9, e104444 (2014). MDM2-ALT1, which consists of only the two terminal coding exons 3 and 12, is the most frequently observed of these splice isoforms. Despite studies characterizing MDM2-ALT1 as a dominant negative regulator of full-length MDM2 and its pervasiveness in various cancers (Sigalas et al., Nat Med, 2, 912-917 (1996); Yu et al., Cancer, 118, 1110-1118 (2012)), there is very little known about the regulation of MDM2 alternative splicing in cancer and under stress.

It is known that MDM2 splicing occurs in cells in response to UV irradiation and cisplatinum treatment in a manner independent of the p53, ATM and ATR status of these cells. Additionally, co-transcriptional regulation of MDM2 splicing has been demonstrated in response to camptothecin. In this case, the disruption of the interaction between the Ewing's Sarcoma Protein (EWS), which interacts with RNA Polymerase II (Pol II) and the spliceosome-associated factor Y-box-binding Protein 1 (YB-1) upon camptothecin treatment results in the uncoupling of transcription and splicing and ultimately the alternative splicing of MDM2. Dutertre et al., Nat Struct Mol Biol, 17, 1358-1366 (2010). However, MDM2 alternative splicing can also occur independently of transcription as demonstrated by in vitro cell-free splicing systems that utilize nuclear extracts from normal and UV or cisplatinum-treated cells. Singh et al., Exp Cell Res, 315, 3419-3432 (2009). Using such in vitro splicing assays in conjunction with a stress-responsive MDM2 minigene, the inventors previously identified conserved positive sequences within intron 11 of MDM2 and binding factors such as FUBP1 that are important for its efficient splicing. Jacob et al., J Biol Chem, 289, 17350-17364 (2014).

SUMMARY

Genotoxic stress induces alternative splicing of the oncogene MDM2, generating MDM2-ALT1, an isoform attributed with tumorigenic properties. However, the mechanisms underlying this event remain unclear. The splicing regulation of MDM2 was explored by utilizing a novel minigene that mimics endogenous MDM2 splicing in response to UV and cisplatinum-induced DNA damage. The inventors have shown that exon 4 or 11 are necessary and sufficient for the damage-specific alternative splicing of the MDM2 minigene and that the splicing factor SRSF1 binds exons 4 and 11 at evolutionarily conserved sites. Interestingly, mutations disrupting this interaction proved sufficient to abolish the stress-induced alternative splicing of the MDM2 minigene. Furthermore, SRSF1 overexpression promoted exclusion of exon 11 while its siRNA-mediated knockdown prevented the stress-induced alternative splicing of endogenous MDM2. Additionally, elevated SRSF1 levels were observed under stress and in tumors correlating with the expression of MDM2-ALT1. Notably, the inventors have demonstrated that MDM2-ALT1 splicing can be blocked by targeting SRSF1 sites on exon 4 or 11 using oligonucleotides (e.g., antisense oligonucleotides). These results present conclusive evidence supporting a negative role for SRSF1 in MDM2 alternative splicing. Importantly, a clear-cut mechanism for the regulation of damage-induced MDM2 splicing has been defined, which presents potential strategies for manipulating MDM2 expression by inhibiting the binding of SRSF1 and SRSF2 to MDM2 exon 4 or 11.

As the chief function of FL-MDM2 is to promote the degradation of p53, inducing or repressing the alternative splicing of MDM2 could prove to be a valuable strategy in promoting the death of cancer cells. For example, antisense oligonucleotide treatment blocking SRSF1 binding in MDM2 exon 4 or 11 would promote a decrease in the MDM2-ALT1 alternatively-spliced transcript, allowing more full-length MDM2 to degrade mut-p53 or block the p53-independent oncogenic functions of MDM2-ALT1. Similarly, SRSF2 binding sites can be targeted to generate more MDM2-ALT1 in wt-p53 cases wherein massive apoptosis is needed to combat the action of other constitutively-active oncogenes. In short, controlling the exact amount of MDM2 alternative splicing using oligonucleotides is an attractive strategy to control p53, both wild-type and mutant in cancer cells. Furthermore, ASO chemistry, as opposed to overexpression of MDM2-FL or siRNA-mediated knock-down of MDM2-ALT1, offers a significant advantage as splicing modulation is very specific and allows for endogenous levels of MDM2 transcription. In addition, these single-stranded RNA molecules are very stable in cells as their chemistry endows them with a mechanism to evade host RNAse degradation.

BRIEF DESCRIPTION OF THE FIGURES

FIGS. 2A-2F provide graphs and images showing the loss of MDM2 exon 11 abolishes stress-responsive alternative splicing of the MDM2 minigene. Chimeric MDM2 minigenes were created by replacing the introns and/or internal exon of MDM2 with corresponding regions from the non-stress-responsive p53 minigene as depicted in the schematics and were subjected to in vitro splicing in nuclear extracts from normal (N) or cisplatinum (C) treated cells. Percentage of the skipped splicing product 3.12 for the various chimeric minigenes is represented graphically for three independent experiments with error bars representing the SEM. *Indicates non-specific band also seen in -ATP controls. ^Indicates probable PCR degradation products. (a) The internal exon 11 and the introns of the MDM2 3-11-12s minigene were removed and replaced with exon 8 and the introns from the p53 minigene. The damage responsive alternative splicing of the MDM2 minigene is abolished and there is no significant difference between the percentage of 3.12 skipped product between normal and damaged conditions (n=3). However, statistically significant changes in the skipping of internal exon 11 (percent 3.12) between the normal and cisplatinum-damaged conditions was observed with the chimeric minigenes. (b) The upstream intron of MDM2 3-11-12s minigene was replaced by the p53 intron 7 (n=3). (c) The downstream intron of MDM2 3-11-12s minigene was replaced by p53 intron 8 (n=3). (d) Both the introns of MDM2 3-11-12s minigene were replaced with p53's introns 7 and 8 (n=3) in a manner similar to the wild-type MDM2 3-11-12s minigene. (e) The chimeric MDM2 minigene in which exon 11 was removed and replaced with p53 exon 8, displayed a loss of the damage-responsive alternative splicing and no statistically significant changes were observed in the percentage of 3.12 product obtained under normal and damaged splicing conditions (n=3). (f) Table summarizing the MDM2 minigene constructs and the status of their damage-responsive splicing.

FIGS. 6A-6D provide graphs and images showing SRSF1 binds predicted exonic splicing enhancer site (SEQ ID NO: 2) in MDM2 exon 11 (SEQ ID NO: 1). (A) ESEfinder 3.0 was used to predict binding sites for SRSF1 (grey box). Mutations were made in the MDM2 3-11-12s minigene (black box) to lower the predicted ESE value. (B) Synthesized oligonucleotides, both wild-type and mutant, were conjugated to agarose beads and incubated in normal and cisplatinum-treated HeLa S3 nuclear extract and washed. Proteins were then eluted by heat and subjected to SDS-PAGE analysis to examine differentially-bound proteins. SRSF1 is capable of binding wild-type oligonucleotides (W) in normal (N, NOR) and cisplatinum-damaged (C, CIS) HeLa S3 nuclear extract (NE) and displays diminished binding to mutant (M) oligonucleotides. Representative data of triplicate experiments is shown. (C) Splicing reactions were pre-incubated with (WT or MUT) or without oligonucleotides (-OLIGO) in the presence of cisplatinum-damaged HeLa S3 nuclear extract. At 1 h the MDM2 3-11-12s minigene was added to reactions and spliced for an additional 2 h. RNA was extracted and subjected to a radioactive RT-PCR using a minigene- and gene-specific primer. PCR products were run on a 4% Native-PAGE gel and spliced products were visualized by autoradiography. (D) The bar graphs represent the percentage of 3.12 skipped product obtained from three independent experiments under each condition and the error bars represent SEM. The wild-type oligonucleotide binds SRSF1 and rescues the damage-induced alternative splicing of the MDM2 3-11-12s minigene (n=3).

FIGS. 7A-7C provide graphs and images showing oligonucleotides that encompass the SRSF1 binding sites can inhibit formation of MDM2-ALT1. (A) Schematic of SRSF1-specific oligonucleotide in MDM2 exon 11 (SEQ ID NO: 1). (B) Transfection of oligonucleotides (#1, #2) in MCF-7 cells rescue skipping of endogenous MDM2 in a dose-dependent manner upon treatment with 50 J/m$^2$ ultra-violet (UVC) for 24 h as compared to a non-specific control (NS). RNA was extracted, reverse transcribed, and subjected to a nested PCR. PCR products were separated on a 1.5% agarose gel and spliced products were visualized by UV imaging. Experiments were repeated three times with consistent results. (C) The bar graphs represent the percentage of 3.12 skipped product obtained from three independent experiments under each condition and the error bars represent SEM. Transfection of oligonucleotide 1 (SEQ ID NO: 3) and oligonucleotide 2 (SEQ ID NO: 4) were sufficient to ablate induction of endogenous MDM2-ALT1 under UV-damaged conditions at a concentration at 500 nM, whereas the non-specific oligonucleotide had no effect (n=3).

FIGS. 9A-9D provide a scheme and images showing binding by oligonucleotides (e.g., antisense oligonucleotides) to exon 11. (A) Schematic of MDM2 exon 11 (box; SEQ ID NO: 1) and the locations of SRSF1 and SRSF2 binding sites. Sequences of ASOs are depicted above (lines) and correspond to sequences provided in Table 1. (B) Evidence that ASO1 (SEQ ID NO: 3) can induce skipping of exon 11 of an MDM2 minigene containing exons 3, 11, and 12 as compared to non-specific antisense oligonucleotide (NS-ASO). While ASO1 (SEQ ID NO: 3) does extend into the SRSF1 binding site, it behaves as predicted in that it causes the skipping of exon 11. However, it is not as potent as ASO3 (SEQ ID NO: 5), which may be due to the overlap with SRSF1. (C) Evidence that OLIGOs 1 (SEQ ID NO: 6) and 2 (SEQ ID NO: 7) can rescue skipping of endogenous MDM2 in a dose dependent manner under UV stress as compared to NS oligonucleotide. (D) Evidence that ASO3 (SEQ ID NO: 5) can induce skipping of endogenous MDM2 in a dose dependent manner under normal conditions as compared to NS-ASO.

FIGS. 13A-13C provide a scheme, image, and chart showing the MDM2 3-4-12s minigene excludes exon 4 under stress. A. Schematic of exon 4 of MDM2 with predicted bindings for SRSF2 (green) and SRSF1 (red). B. MCF7 cells with the MDM2 3-4-12s minigene, treated under normal UVC (UV) and cisplatinum (CIS) conditions, and subjected to a RT-PCR. Percentage of 3.12 product shown below. C. ESEfinder 3.0 predicted matrix scores of regulators SRSF1 and SRSF2 in MDM2 exon 4.

DETAILED DESCRIPTION

Figures 1A, 1B:
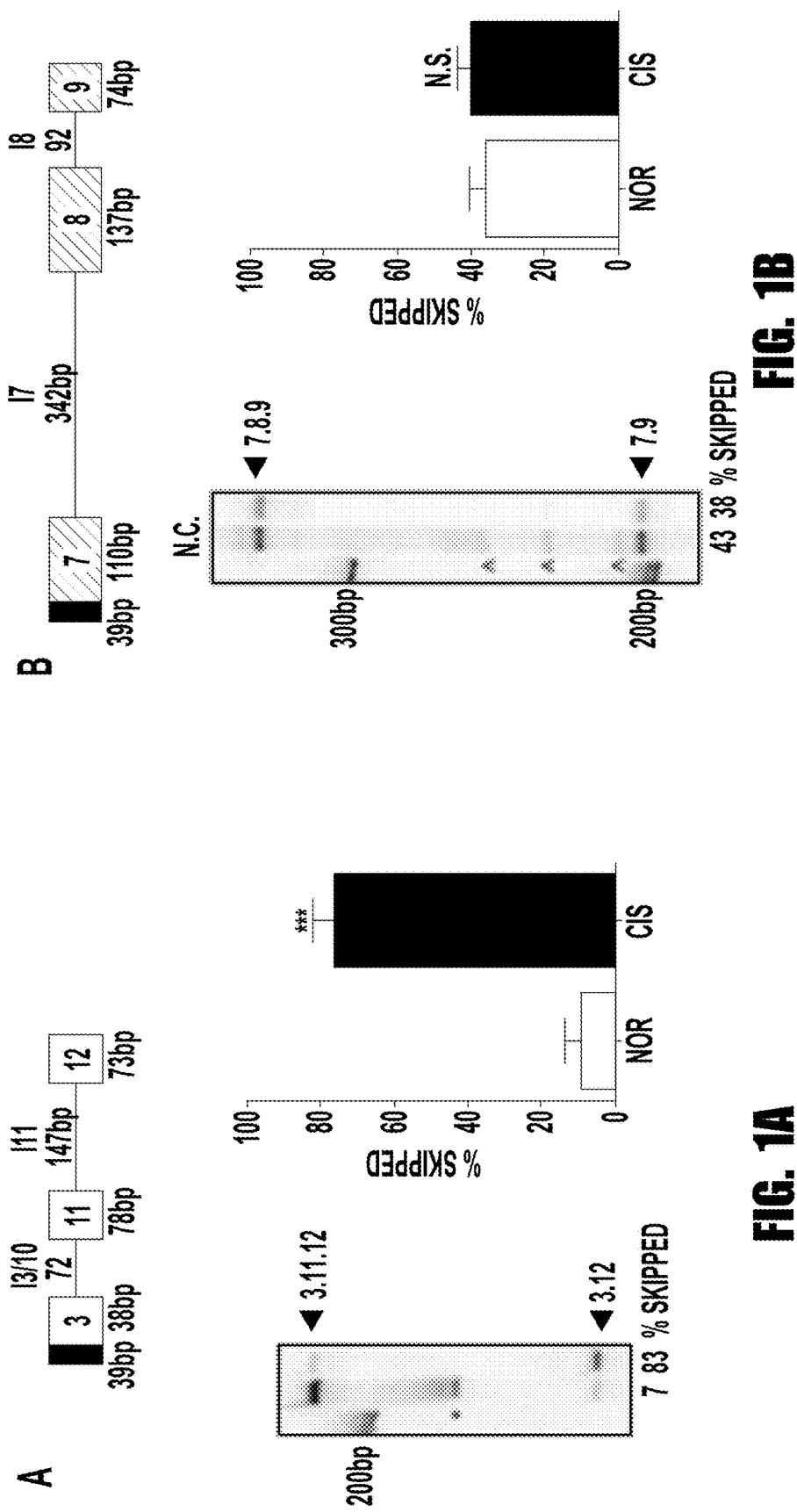
FIGS. 1A and 1B provide graphs and images showing the MDM2 3-11-12s minigene undergoes damage-induced exon 11 skipping in an in vitro splicing system while a control p53 7-8-9 minigene remains unresponsive. (a) A minimal MDM2 3-11-12s minigene constructed to assess the elements essential for the generation of MDM2-ALT1 alternative splicing was derived from the previously described MDM2 3-11-12 minigene, which is responsive to stress-induced alternative splicing. The schematic represents the 3-11-12s minigene and the sizes depicted reflect the length of the exonic and intronic regions of the minigene construct and are inclusive of the Flag-tag and the intervening region (cloning sites) of the pCMV-tag2B vector at the 5' end of the minigene construct. In vitro transcribed RNA obtained from the minigenes was subjected to a cell-free in vitro splicing assay using nuclear extracts from either untreated (N, NOR) or cisplatinum-treated Hela S3 cells (C, CIS). RNA was isolated, reversed transcribed, and subjected to a 25-cycle PCR using γ-32P-radioactively-labeled Flag primer and gene-specific reverse primers. The MDM2 minigene predominantly skips internal exon 11 when spliced in nuclear extracts from cisplatinum-treated cells, but not in nuclear extract from normal cells. The bar graphs represent the percentage of 3.12 skipped product obtained from three independent in vitro splicing experiments under each condition and the error bars represent standard error mean (SEM). The difference in the percentage of 3.12 product between normal and damaged splicing conditions is statistically significant (n=3). *Indicates non-specific band also seen in -ATP controls. ^Indicates probable PCR degradation products. (b) Damage-responsive alternative splicing is transcript-specific. A p53 7-8-9 minigene shows no changes in splicing patterns between the normal and damaged nuclear extract (n=3). The sizes of the minigene depicted in the schematic are reflective of the flag-tag and vector-specific regions at the 5' end of the minigene construct in a manner similar to the 3-11-12s minigene.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein and in the appended claims, the singular forms "a", "and", and "the" include plural referents unless the context clearly dictates otherwise. Thus, for example, reference to "a sample" also includes a plurality of such samples and reference to "the splicing regulator protein" includes reference to one or more protein molecules, and so forth.

As used herein, the term "about" refers to +/−10% deviation from the basic value.

As used herein the term "nucleic acid" or "oligonucleotide" refers to multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). The term shall also include polynucleosides (i.e. a polynucleotide minus the phosphate) and any other organic base containing polymer. Purines and pyrimidines include but are not limited to adenine, cytosine, guanine, thymidine, inosine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Other such modifications are well known to those of skill in the art. Thus, the term nucleic acid also encompasses nucleic acids with substitutions or modifications, such as in the bases and/or sugars.

The term "base" encompasses any of the known base analogs of DNA and RNA. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides.

The term "antisense oligonucleotide", as used herein, refers to a single-stranded oligonucleotide with a base sequence complementary to a segment of another oligonucleotide that can specifically bind to the target oligonucleotide and inhibit its activity. Antisense oligonucleotides include antisense RNA and antisense DNA, as well as other types of antisense molecules described herein.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Peptide" and "polypeptide" are used interchangeably herein and refer to a compound made up of a chain of amino acid residues linked by peptide bonds. An "active portion" of a polypeptide means a peptide that is less than the full length polypeptide, but which retains measurable biological activity and retains biological detection.

As used herein, the term "tumor" refers to any neoplastic growth, proliferation or cell mass whether benign or malignant (cancerous), whether a primary site lesion or metastases.

As used herein "therapeutically effective amount" refers to an amount of a composition that relieves (to some extent, as judged by a skilled medical practitioner) one or more symptoms of the disease or condition in a mammal Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction of the undesirable proliferating cells with minimal destructive effects on normal cells. In accordance with the present invention, desired mechanisms of treatment at the cellular include, but are not limited to one or more of apoptosis, cell cycle arrest, cellular differentiation, or DNA synthesis arrest. A subject at risk is a subject who has been determined to have an above-average risk that a subject will develop cancer, which can be determined, for example, through family history or the detection of genes causing a predisposition to developing cancer.

The term "subject," as used herein, refers to a species of mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

Unless defined otherwise, all technical and scientific terms used herein have the same meaning as commonly understood by one of ordinary skill in the art to which this invention belongs.

In one aspect, the invention provides a method of treating cancer in a subject in need thereof, comprising administering a therapeutically effective amount of an oligonucleotide that inhibits the binding of splicing regulator SRSF1 or SRSF2 to MDM2 exon 11 (SEQ ID NO: 1). As described herein, inhibiting the binding of splicing regular SRSF1 or SRSF2 to MDM2 exon 4 or 11 blocks MDM2-ALT1 splicing, leading to p53 upregulation, which causes apoptosis, cell cycle arrest, and an anticancer effect. In some embodiments, the oligonucleotide is an antisense oligonucleotide. In other embodiments, the oligonucleotide is a sense oligonucleotide that acts as a molecular competitor for binding.

Oligonucleotides such as sense and antisense oligonucleotides are tools for use in inhibiting the expression of target genes in a sequence-specific manner and have found use in functional genomics, target validation, and for therapeutic purposes. Different types of anti-mRNA strategies include, for example, the use of single stranded antisense-oligonucleotides, the triggering of RNA cleavage through catalytically active oligonucleotides referred to as ribozymes, RNA interference induced by small interfering RNA molecules, and oligonucleotides that compete for binding. The successful use of antisense oligonucleotides may depend, for example, on identifying accessible sites of the target RNA for oligonucleotide binding, protecting the antisense oligonucleotides from nucleolytic attack, preventing their cellular uptake, and providing for the correct intracellular localization. Some success has been shown with chemically modified nucleotides, for example, alkyl modifications at the 2' position of the ribose. These chemically modified nucleotides have shown improved serum stability, higher target affinity and low toxicity. Another aspect of the invention provides antisense oligonucleotides, and compositions including antisense oligonucleotides.

In some embodiments, the oligonucleotide inhibits the binding of the splicing regulator SRSF1 to MDM2 exon 4 or 11, while in other embodiments the oligonucleotide inhibits the binding of splicing regular SRSF2 to MDM2 exon 4 or 11. In some embodiments, exon 4 is specifically targeted, while in other embodiments exon 11 is specifically targeted. Binding of the splicing regulators to MDM2 exons 4 or 11 can occur to a varying degree. In some embodiments, inhibition of binding represents inhibition by at least 25%, at least 30%, at least 80%, at least 100 fold, or in some embodiments at least 1,000 fold to the level of binding that would occur in the absence of the oligonucleotide.

Splicing regulators SRSF1 and SRSF2 bind to different regions of the MDM2 exon 11, and these regions have been identified. Accordingly, in some embodiments, all or a portion of the antisense oligonucleotide can be selected to be complementary to the region within the MDM2 exon 4 or 11 where binding of SRSF1 or SRSF2 occurs. For example, the region to which binding of the splicing regular SRSF1 occurs includes the nucleotide sequence GGCAGGGGA, and therefore in this embodiment a portion of the antisense oligonucleotide is complementary to the nucleotide sequence GGCAGGGGA. Alternately, the region to which binding of the splicing regulator SRSF2 occurs includes the nucleotide sequence AGTTACTG or AGATCCTG, and therefore in this embodiment a portion of the antisense oligonucleotide is complementary to the nucleotide sequence AGTTACTG or AGATCCTG.

In some embodiments, oligonucleotides having the same sequence as a region of MDM2 exon 4 or 11 where binding of SRSF1 or SRSF2 to a region within the MDM2 exon 4 or 11 (i.e., competitive inhibitors) can be used to inhibit binding. In this case, inhibition occurs not through blocking the binding site, but instead by providing competing binding sites that decrease the level of effective binding.

The inventors have identified a number of specific oligonucleotides that inhibit the binding of splicing regulator SRSF1 or SRSF2 to MDM2 exon 11. These oligonucleotides are shown in Table 1. These oligonucleotides can block binding by either SRSF1 or SRSF2. Oligonucleotides OLIGO1 or OLIGO2 block or interfere with the binding of splicing regulator SRSF1, while antisense oligonucleotides ASO1, ASO2, and ASO3 block the binding of splicing regular SRSF2.

TABLE 1

Oligonucleotides that inhibit the binding of splicing regulator SRSF1 or SRSF2 to MDM2 exon 11

| Designation | 5' to 3' nucleotide sequence |
|---|---|
| ASO1 | CUGCCUGAUACACAGUAACU (SEQ ID NO: 3) |
| ASO2 | UCCCCUGCCUGAUACACAGU (SEQ ID NO: 4) |
| ASO3 | UUUCAGGAUCUUCUUCAAAU (SEQ ID NO: 5) |
| OLIGO1 | GUAUCAGGCAGGGGAGAGUG (SEQ ID NO: 6) |
| OLIGO2 | CAGGCAGGGGAGAGUGAUAC (SEQ ID NO: 7) |

In preferred embodiments, the oligonucleotide can have a sequence selected from SEQ ID NOs: 3-7. In other embodiments, the sequence is at least 80% identical, at least 90% identical, at least 95% identical, or at least 99% identical to any of SEQ ID NOs: 3-7. Typically, the oligonucleotide is capable of specifically hybridizing to a portion of SEQ ID NO: 1. The portion of SEQ ID NO: 1 to which the antisense oligonucleotide specifically hybridizes can include 5 to 25, 5 to 20, 5 to 15, or 20 to 20 nucleotides. One of ordinary skill in the art will understand that degenerate or modified nucleotides are further contemplated but must also be capable of specifically hybridizing to the sequence of SEQ ID NO: 1. For example, an oligonucleotide could differ from the complementary sequence by three nucleotides, two nucleotides, or preferably one nucleotide, although oligonucleotides having the complementary sequence itself are most preferred.

With respect to single stranded nucleic acids, particularly antisense oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a RNA molecule, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

Suitable oligonucleotides can be unmodified or chemically modified single-stranded oligonucleotides capable of specifically hybridizing to MDM2 exon 4 or 11. Suitable sense or antisense oligonucleotides can be from 5 to 30 bases in length, from 10 to 30 bases in length, preferably from 12 to 25 bases in length. In some embodiments, the sense or antisense oligonucleotides are from 12 to 19 bases in length. Preferred oligonucleotides are phosphorothioate-backboned oligonucleotides, which are a type of artificial polynucleotide having greater stability.

Suitable oligonucleotides (e.g., antisense oligonucleotides) for use in accordance with the invention can be composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides, for instance, the ability to penetrate a cell membrane, good resistance to extra- and intracellular nucleases, high affinity and specificity for the nucleic acid target.

Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA.

In some embodiments, deoxyribonucleotide phosphodiester oligonucleotides are suitable for use in accordance with the invention. Methylphosphonate oligonucleotides are non-charged oligomers, in which a nonbridging oxygen atom is replaced by a methyl group at each phosphorus in the oligonucleotide chain. The phosphorothioates in the phosphorothioate diastereomer have improved nuclease stability. Another class of antisense oligonucleotides contains alkyl modifications at the 2' position of the ribose. 2'-O-methyl and 2'-O-methoxy-ethyl RNA are members of this class. 2'-O-alky RNA oligonucleotides do not recruit RNase H, their antisense effect is due, for example, to a steric block of translation. Other antisense oligonucleotides modifications may include, for example, C-5 propyne, 2'-O-aminopropyl, and dipyridophenazine-DPPZ. These oligonucleotides form high melting heteroduplexes with targeted mRNA and induce an antisense effect by a non-RNase H-dependent mechanism.

Suitable oligonucleotides also include embodiments that do not possess the natural phosphate-ribose backbone. Peptide Nucleic Acids (PNAs) are nucleic acid analogues that contain an uncharged, flexible, polyamide backbone comprised of repeating N-(2-aminoethyl) glycine units to which the nucleobases are attached via methylene carbonyl linkers. These oligomers can form very stable duplexes or triplexes with nucleic acids: single or double-strand DNA or RNA. The property of high-affinity nucleic acid binding can be explained by the lack of electrostatic repulsion because of the absence of negative charges on the PNA oligomers. Because PNAs are not substrates for the RNase H or other RNases, the antisense mechanism of PNAs depends on steric hindrance. PNAs can also bind to DNA and inhibit RNA polymerase initiation and elongation, as well as the binding and action of transcription factors, such as nuclear factor κB. PNAs can also bind mRNA and inhibit splicing or translation initiation and elongation.

Cancer Treatment

The invention provides a method of treating cancer in a subject in need thereof using the oligonucleotides described herein. The term "cancer" refers to a proliferative disorder caused or characterized by a proliferation of cells which have lost susceptibility to normal growth control. Cancers of the same tissue type usually originate in the same tissue, and may be divided into different subtypes based on their biological characteristics. Four general categories of cancer are carcinoma (epithelial cell derived), sarcoma (connective tissue or mesodermal derived), leukemia (blood-forming tissue derived) and lymphoma (lymph tissue derived). Over 200 different types of cancers are known, and every organ and tissue of the body can be affected. Specific examples of cancers that do not limit the definition of cancer can include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. Alternatively, a cancer can be multicentric or of unknown primary site (CUPS).

Figures 14A, 14B, 14C:
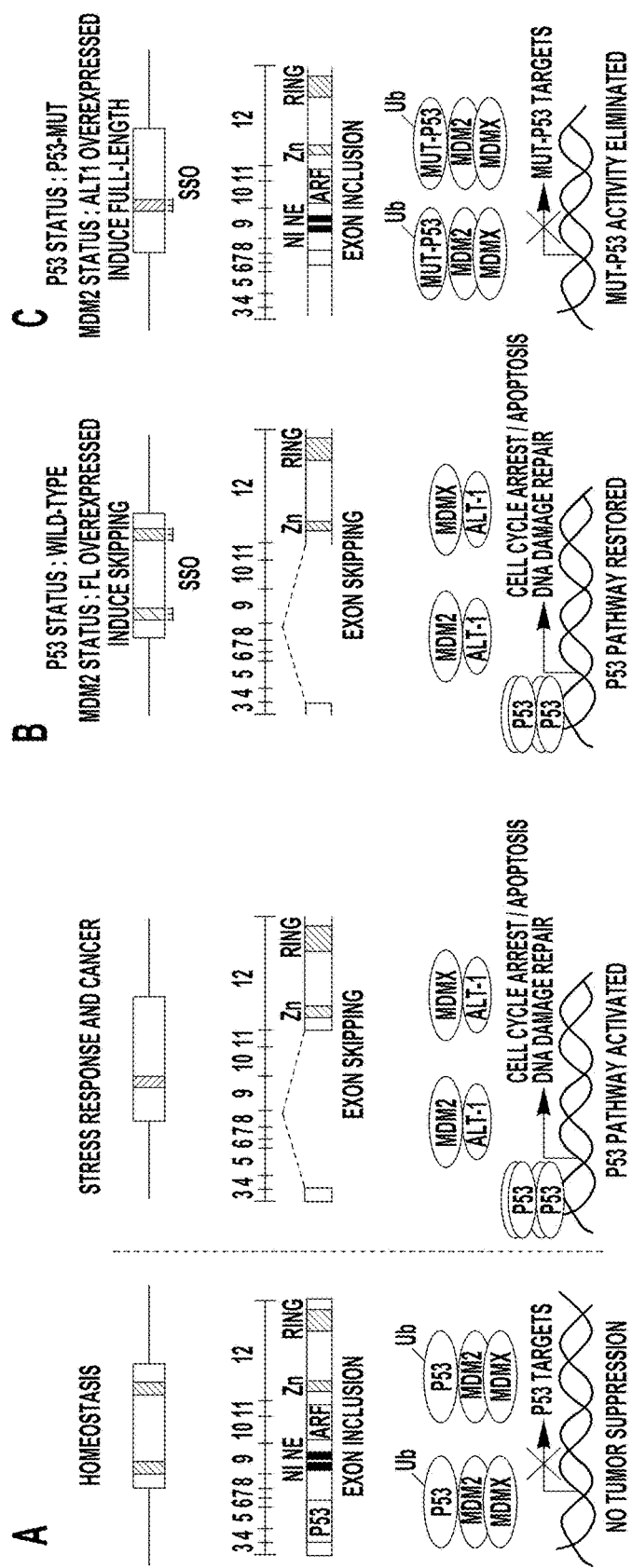
FIGS. 14A-14C provide schematic diagrams showing Full-length MDM2 is tumor suppressive while MDM2-ALT1 activates p53 tumor suppressor activity. Splice Switching Oligonucleotides (SSOs) can be used to modulate MDM2 alternative splicing and thus p53 activity. A. Positive splicing elements in the exon of MDM2 (depicted as green bars) facilitate inclusion of all 12 exons in the MDM2 full-length transcript. Structurally, the MDM2 protein is characterized by a N-terminal p53 binding domain (p53) and nuclear import (NI) and export signals (NE). A centrally located acidic domain (ARF) functions as the binding domain for tumor suppressor gene, ARF. ARF binds to MDM2 and inactivates its ability to target p53 for degradation, acting as an activator of p53 function. The C-terminus of MDM2 is characterized by a RING domain, which has been shown to be important for binding to RNA and the protein's E3 ubiquitin ligase activity. The RING domain has additionally been shown to be important for MDM2 homodimerization as well as for interacting with MDM4 (MDMX) another related regulator of p53. Alternative splicing of MDM2 as induced by DNA damage and in cancer activates p53 tumor suppressive activity by binding and sequestering the negative regulators of p53, MDM2 and MDM4. B. In tumors whose p53 activity is inactivated by overexpression of full-length MDM2, inducing alternative splicing using SSOs (antisense) to target positive splicing elements would induce MDM2-ALT1 and provide a way to reactivate p53 activity. C. Expression of the damage-induced alternative isoform of MDM2 facilitates the expression of mutant p53 and can drive oncogenesis. Under this circumstance, it would be therapeutically beneficial to reinstate full-length MDM2 splicing to inactivate mutant p53 activity using an SSO (sense) to inhibit SRSF1 binding to MDM2.

In some embodiments the cancer comprises wild-type tumor suppressor protein p53, while in other embodiments the cancer comprises a mutant form of tumor suppressor protein p53. SRSF1 is a negative regulator, and as a result cancer can result from a mutation of tumor suppressor p53. SRSF2 is a positive regulator, which if blocked leads to activation of tumor suppressor protein p53. Presence of mutant or wild-type versions of tumor suppressor protein p53 therefore result in tumors receptive to affects targeting either the SRSF1 or SRSF2 splicing regulators. See FIGS. 14A-14C.

Treatment includes therapy that provides a result which substantially decreases the level or expression of, including for example, an about 20% reduction, preferably an about 25% reduction, more preferably an about 30% reduction, even more preferably an about 33% reduction, even more preferably an about 50% reduction, even more preferably an about 67% reduction, even more preferably an about 80% reduction, even more preferably an about 90% reduction, even more preferably an about 95% reduction, even more preferably an about 99% reduction, even more preferably an about 50 fold reduction, even more preferably an about 100 fold reduction, even more preferably an about 1,000 fold reduction, even more preferably an about 10,000 fold reduction, and most preferable complete inhibition of binding between SRSF1 or SRSF2 and MDM2 exon 11.

Methods in accordance with the invention include administration of the oligonucleotides alone, or combination therapies wherein the animal is also undergoing one or more cancer therapies selected from the group consisting of surgery, chemotherapy, radiotherapy, thermotherapy, immunotherapy, hormone therapy and laser therapy.

In general any combination therapy will include one or more of chemotherapeutics, targeting agents like antibodies; kinase inhibitors; hormonal agents and the like. Combination therapies can also include conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, anti-cancer agents that are well known in the art and can be used as a treatment in combination with the compositions described herein include, but are not limited to As used herein, a first line "chemotherapeutic agent" or first line chemotherapy is a medicament that may be used to treat cancer, and generally has the ability to kill cancerous cells directly.

Examples of chemotherapeutic agents include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Whereas, electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Oligonucleotide Formulation and Administration

In order for an oligonucleotide (e.g., antisense oligonucleotide) to down-regulate gene expression, it must penetrate into the targeted cells. Uptake occurs through active transport, which in turn depends on temperature, the structure and the concentration of the oligonucleotide, and the cell line. Without desiring to be bound by any theories of the mechanism of action, it is believed that adsorptive endocytosis and fluid phase pinocytosis are the major mechanisms of oligonucleotide internalization, with the relative proportions of internalized material depending on oligonucleotide concentration. At relatively low oligonucleotide concentration, it is likely that internalization occurs via interaction with a membrane-bound receptor. At relatively high oligonucleotide concentration, these receptors are saturated, and the pinocytotic process assumes larger importance.

The use of vectors in delivery of oligonucleotides in accordance with the invention is optional. Clinical trials with antisense oligonucleotides are carried out with naked oligonucleotides.

However to improve cellular uptake and oligonucleotide spatial and temporal activity, a range of techniques and vectors have been developed. Suitable vectors include liposomes, which are vesicular colloid vesicles generally composed of bilayers of phospholipids and cholesterol. Liposomes can be neutral or cationic, depending on the nature of the phospholipids. The oligonucleotide can be easily encapsulated in the liposome interior, which contains an aqueous compartment, or be bound to the liposome surface by electrostatic interactions. These vectors, because of their positive charge, have high affinity for cell membranes, which are negatively charged under physiological conditions. As these vectors use the endosomal pathway to deliver oligonucleotides into cells, certain "helper" molecules have been added into the liposomes to allow the oligonucleotides to escape from the endosomes; these include species such as chloroquine and 1,2-dioleoyl-sn-glycero-3-phosphatidylethanolamine These "helper" molecules ultimately induce endosomal membrane destabilization, allowing leakage of the oligonucleotide, which then appears to be actively transported in high concentration to the nucleus. Many commercial vectors, such as Lipofectin and compounds known collectively as Eufectins, Cytofectin, Lipofectamine, etc., are commonly used in laboratory research studies. With some of these delivery vehicles, and under defined conditions, oligonucleotide concentrations of <50 nm may be successfully used. The use of other cationic polymers, including, e.g., poly-L-lysine, PAMAM dendrimers, polyalkylcyanoacrylate nanoparticles, CPPs, and polyethyleneimine, are also suitable for use in accordance with the invention.

All of these cationic delivery systems internalize oligonucleotides via an endocytosic mechanism. To avoid the resulting compartmentalization problems, consideration has been given to modulating plasma membrane permeability. By using basic peptides, one can increase oligonucleotide passage through the plasma membrane by a receptor- and transporter-independent mechanism. As these peptides have membrane translocation properties, covalent coupling with an oligonucleotide can increase the latter's penetration into the cell, delivering them directly into the cytoplasm and hence ultimately the nucleus.

An additional suitable approach to oligonucleotide internalization is to generate transient permeabilization of the plasma membrane and allow naked oligonucleotides to penetrate into the cells by diffusion. This approach involves the formation of transitory pores in the membrane, induced either chemically by streptolysin O permeabilization, mechanically by microinjection or scrape loading, or produced by electroporation.

Contemplated oligonucleotides and conjugates thereof can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present inventions are generally provided in a formulation with a carrier, such as a pharmaceutically acceptable carrier. Typically, the carrier will be liquid, but also can be solid, or a combination of liquid and solid components. The carrier desirably is a physiologically acceptable (e.g., a pharmaceutically or pharmacologically acceptable) carrier (e.g., excipient or diluent). Physiologically acceptable carriers are well known and are readily available. Suitable pharmaceutical excipients include stabilizers, antioxidants, osmolality adjusting agents, buffers, and pH adjusting agents. Suitable additives include physiologically biocompatible buffers, additions of chelants or calcium chelate complexes, or, optionally, additions of calcium or sodium salts. Pharmaceutical compositions can be packaged for use in liquid form, or can be lyophilized Preferred physiologically acceptable carrier media are water, buffered water, normal saline, 0.4% saline, 0.3% glycine, hyaluronic acid and the like. The choice of carrier will be determined, at least in part, by the location of the target tissue and/or cells, and the particular method used to administer the composition.

The composition can be formulated for administration by a route including intravenous, intraarterial, intramuscular, intraperitoneal, intrathecal, epidural, topical, percutaneous, subcutaneous, transmucosal (including, for example, pulmonary), intranasal, rectal, vaginal, or oral. The composition also can comprise additional components such as diluents, adjuvants, excipients, preservatives, and pH adjusting agents, and the like.

Formulations suitable for injectable administration include aqueous and nonaqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, lyoprotectants, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, or tablets.

In preferred embodiments, the oligonucleotides can be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the antisense oligonucleotides can be prepared by such methods as described in Rezler et al., J. Am. Chem. Soc. 129(16): 4961-72 (2007); Samad et al., Curr. Drug Deliv. 4(4): 297-305 (2007); and U.S. Pat. Nos. 4,485,045 and 4,544,545. Liposomes with enhanced circulation time are disclosed in U.S. Pat. No. 5,013,556. Albumin nanoparticles are particularly preferred in the compositions of the present invention.

Particularly useful liposomes can be generated by, for example, the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polynucleotides of the present invention can be conjugated to the liposomes using methods as described in Werle et al., Int. J. Pharm. 370(1-2): 26-32 (2009).

The invention further provides for the use of Cell-Penetrating Peptides (CPPs) to facilitate the delivery of the antisense molecules disclosed herein. CPPs are peptides that are able to efficiently penetrate cellular lipid bilayers. Because of this feature, they can be used to obtain alterations in gene expression. CPPs have been utilized in in vivo and in vitro experiments as delivery vectors for different bioactive cargoes. In particular, CPPs have been used as vectors for multiple effectors of gene expression such as oligonucleotides for antisense, siRNA (small interfering RNA) and decoy dsDNA (double-stranded DNA) applications, and as transfection agents for plasmid delivery. Any suitable conjugation method may be employed to couple the CPP and the oligonucleotide (Heitz et al., Br J. Pharmacol. 2009 157(2): 195-206.) Suitable CPPs include, but are not limited to, Tat, Penetratin, Transportan, VP-22, MPG, Pep-1, MAP, PPTG1, SAP, Oligoarginine, SynB, Pvec, and hCT (9-32) (Heitz et al., Br J. Pharmacol. 2009 157(2):195-206.).

In other embodiments, a composition can be delivered using a natural virus or virus-like particle, a dendrimer, carbon nanoassembly, a polymer carrier, a paramagnetic particle, a ferromagnetic particle, a polymersome, a filomicelle, a micelle or a lipoprotein.

Administration into the airways can provide either systemic or local administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, rectal or vaginal suppositories, mouthwashes, rapidly dissolving tablets, or lozenges. For transdermal administration, the active compounds are formulated into ointments, salves, gels, foams, or creams as generally known in the art.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl) methylacrylamide] and the like. Particular formulations using drug delivery systems can be in the form of liquid suspensions, ointments, complexes to a bandage, collagen shield or the like.

Pharmaceutical compositions of the invention can be administered in a single dose or in multiple doses. Where the administration of such a composition is by infusion, the infusion can be a single sustained dose or can be delivered by multiple infusions. Injection of the agent can be directly into the tissue at or near the site of aberrant target gene expression. Multiple injections of the agent can be made into the tissue at or near the site.

Dosage levels on the order of about 1 ug/kg to 100 mg/kg of body weight per administration are useful in the treatment of a disease. In regard to dosage, an compositions of the present invention can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antisense composition per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antisense composition per kg of bodyweight. The unit dose, for example, can be administered by injection (e.g., intravenous or intramuscular, intrathecally, or directly into an organ), inhalation, or a topical application.

One skilled in the art can also readily determine an appropriate dosage regimen for administering the antisense composition of the invention to a given subject. In some embodiments, the compositions are administered once or twice daily to a subject for a period of from about three to about twenty-eight days, more preferably from about seven to about ten days. In further embodiments, the unit dose is administered less frequently than once a day, e.g., less than every 2, 4, 8 or 30 days. In other embodiments, the unit dose is not administered with a frequency (e.g., not a regular frequency). In another embodiment, the unit dose is not administered with a frequency (e.g., not a regular frequency). In other embodiments, the antisense composition can be administered to the subject once, as a single injection or deposition at or near the site on unwanted target nucleic acid expression. Because oligonucleotide agent-mediated up-regulation can persist for several days after administering the antisense composition, in many instances, it is possible to administer the composition with a frequency of less than once per day, or, for some instances, only once for the entire therapeutic regimen.

Where a dosage regimen comprises multiple administrations, it is understood that the effective amount of antisense composition administered to the subject can include the total amount of antisense composition administered over the entire dosage regimen. One skilled in the art will appreciate that the exact individual dosages may be adjusted somewhat depending on a variety of factors, including the specific antisense composition being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration.

The following examples are included for purposes of illustration and are not intended to limit the scope of the invention.

EXAMPLES

Example 1

Splicing Factor SRSF1 Negatively Regulates Alternative Splicing of MDM2 Under Damage The inventors have identified repressive elements in MDM2 exon 11 (SEQ ID NO: 1) that facilitate its damage-inducible alternative splicing. Using a SELEX-based bioinformatics program, the predicted binding sites for SRSF1 in this regulated exon were identified. The binding of SRSF1 to this site is increased under damage and its mutation is sufficient to ablate damage-induced exon 11 exclusion in a three-exon minigene system both in vitro and in cell-based transfection assays. Additionally the inventors show that blocking this binding site on endogenous MDM2 is capable of preventing the generation of MDM2-ALT1 under stress. Altogether the data address SRSF1 as a critical modulator of endogenous MDM2 alternative splicing, providing necessary information in the regulation of this important oncogene and a potential therapeutic target for intervention in the myriad cancers in which MDM2-ALT1 is observed.

Material and Methods

Plasmids, Protein Expression Constructs

LacZ cDNA was cloned into the BglII-XhoI sites of the Cre-inducible pCCALL2 vector whose β-galactosidase and neomycin resistance cassettes were previously excised by Cre recombinase to facilitate constitutive expression of the corresponding downstream cDNA. HNRNPL cDNA was cloned into the pcDNA3 vector. The p3x-FLAG hnRNPF and pFRT/TO/HIS/FLAG/HA-hnRNPR plasmids were purchased commercially from Addgene. The FLAG-GFP-hnRNPU construct was provided as a gift kind from Dr. Patrick Calsou. The FLAG-hnRNPD construct was provided as a kind gift from Dr. Stephen Kolb. The T7-SRSF1 construct was provided as a kind gift from Adrian Krainer.

Minigene Constructs

The MDM2 3-11-12s minigene was constructed by truncating exon 3 (from 85 nt to include only the 38 nt at its 3' end), exon 12 (from 229 nt to include only the 73 nt at the 5' end), the upstream intron 3/10 (from 167 nt to 72 nt retaining 19 nt at its 5' end and 53 nt of the 3' end) and the downstream intron 11 (from 316 nt to 147 nt including only 79 nt at the 5' end and 68 nt of the 3' end) of the previously described MDM2 3-11-12 stress-responsive minigene (Singh et al., Exp Cell Res, 315, 3419-3432 (2009), referred to herein as Singh et al., 2009). To assemble this minigene into the pCMV-tag2B vector, a strategy similar to the one described for the construction of the 3-11-12 minigene (Singh et al., 2009), was adopted. Using restriction sites engineered into the 5' ends of PCR products, the 3' end of intron 11 (68 nt region) and exon 12 (the complete exon 12 from the 3-11-12 minigene) were first cloned into the EcoR1-Xho1 sites of the pCMV-Tag2B vector using the following primers: For: 5' TCGAATTCGCTAGCATTCCTGTGACTGAGCAG 3' (SEQ ID NO: 8) and rev: 5' TAACTCGAGCCTCAACACATGACTCT 3' (SEQ ID NO: 9). Following this, exon 12 was truncated at its 3' end first by restriction digest of the ApaI site in the multiple cloning site (MCS) of the pCMV-tag2B vector and the ApaI site native to exon 12 to release the 3' fragment of exon 12. Following this, the construct was relegated to obtain the short exon 12 with only 73 nt at the 5' end. Subsequently, the 3' end of intron 3/10 (53 nt), exon 11 (78 nt) and the 5' end of intron 11 (79 nt) were amplified using primers (For: 5' GCCTGCAGCTGATTGAAGGAAATAGGGCG (SEQ ID NO: 10) and Rev: 5' AGGGAATTCGAAGCTAGA-TATAGTCT 3' (SEQ ID NO: 11)) that bear PstI and EcoRI sites at their 5' ends and the PCR product thus obtained was cloned into the PstI-EcoRI sites of construct bearing the other end of intron 11 and truncated exon 12. Finally, using a similar approach, the exon 3 (38 nt) and the 5' end of intron 3/10 (19 nt) were amplified (For: 5' GCGGATCCCCACCT-CACAGATTCCAGCTTCGG 3' (SEQ ID NO: 12) Rev: 5' CTGCAGCAAAAATACTAACCAGGGTCTC 3' (SEQ ID NO: 13)) and cloned into the BamHI and PstI sites located on the MCS of the assembly vector containing the rest of the minigene. The construction of the p53 7-8-9 minigene has been described previously in Singh et al., 2009.

Chimeric minigenes: The chimeric minigenes of MDM2 or p53 origin were all constructed by keeping the terminal exons (3 and 12 for the MDM2 and 7 and 9 for the p53 minigenes) intact with respect to their wild-type counterparts. Also, when the intronic regions were being swapped between the MDM2 and p53 minigenes, they did not include their native splice sites (the first 10 and the last 10 nt of each intron were considered as the splice sites and were not included in the intronic region being ligated into the heterologous system). On the other hand, the splice sites were maintained native to the exons (native to either the terminal exons or the internal exon being swapped) as 10 nt in the intron upstream or downstream or flanking the exon. For instance, the exon 11 retained the splice sites native to MDM2 with the flanking 10 nt from the intron 11 and intron 3/10 even when placed in the context of the p53 minigene. A similar condition was maintained when p53 exon 8 was being placed in the MDM2 minigene context. The chimeric minigenes were assembled in the BamHI and HindIII sites of the pCMV-tag2B vector using the Clontech Infusion HD Kit (Catalog Number 638909). The individual elements to be assembled were first amplified using primers (designed using the Infusion HD primer-design tools) with 15 bp overhangs complementary to the elements that will be placed adjacent to them. Following this, the inserts were ligated into the pCMV-Tag2B vector digested with BamHI and HindIII and then transformed into stellar competent cells according the manufacturer's protocols. All clones were verified by DNA sequencing.

Protein Extraction from RMS Tissues

Human tissue samples were obtained from the Cooperative Human Tissue Network, Pediatric Division at Columbus Nationwide Children's Hospital after Institutional Review Board approval. All specimens were snap-frozen and stored at −80° C. The tissue was ground using a mortar and pestle in liquid nitrogen. Protein was extracted using 300 µl of RIPA buffer (150 mM NaCl, 50 mM Tris pH 8.0, 0.5% sodium deoxycholate, 1.0% Triton X-100, 0.1% sodium dodecyl sulfate, 1 mM ethylenediaminetetraacetic acid pH 8.0) and homogenized with a Tissumizer (Tekmar, Cincinnati, Ohio).

RT and Polymerase Chain Reactions

Typical RT reactions were carried out using 1 µg of RNA unless otherwise mentioned. Transcriptor RT enzyme (Catalog No. 03531287001) from Roche Diagnostics (Indianapolis, Ind.) was used for the cDNA synthesis reactions according to the manufacturer's instructions. Polymerase chain reactions (PCRs) for in vitro splicing were performed using Platinum Taq Polymerase (Catalog Number 11304-011) from Life Technologies (Carlsbad, Calif.) and subjected to a 25-cycle PCR using ATP γ-32P-radioactively-labeled Flag primer and gene-specific reverse primers under standard PCR conditions (95° C. 4', 95° C. 0:40, 55° C. 0:30, 72° C. 1', 72° C. 7'). Endogenous MDM2 polymerase chain reactions (PCRs) were performed using Taq Polymerase (Catalog Number D6677) from Sigma-Aldrich (St. Louis, Mo.) using a set of nested primers as previously reported (39). SRSF1 isoform PCRs were performed using Platinum Taq Polymerase (Catalog Number 11304-011) from Life Technologies (Carlsbad, Calif.) and subjected to a 30-cycle PCR using primers (SF2-e3F 5' CACTGGTGTCGTGGAGTTT-GTACGG 3' (SEQ ID NO: 14) and SF2-e4R 5' GGGCA-GGAATCCACTCCTATG 3' (SEQ ID NO: 15)) under standard PCR conditions (94° C. 5', 94° C. 0:30, 62° C. 0:30, 72° C. 2', 72° C. 7'). SRSF1 and CDKN1A qPCRs were performed using TaqMan® Universal PCR Master Mix (Catalog Number 4304437) from Life Technologies (Carlsbad, Calif.) using probes for SRSF1 (Hs001199471), CDKN1A (Hs00355782), and GAPDH (Hs503929097) under standard PCR conditions (95° C. 15', 95° C. 0:15, 60° C. 1') for 40 cycles on a Applied Biosystems 7900HT Fast Real Time PCR system (Life Technologies, Carlsbad, Calif.).

Western Blot Analysis and Antibodies

Cell were lysed in NP-40 buffer and equal amounts of protein were loaded in 6× sodium dodecyl sulfate (SDS) sample buffer onto a sodium dodecyl sulfate-polyacrylamide gel electrophoresis gel (SDS-PAGE) and blotted onto a polyvinylidene difluoride (PVDF) membrane and analyzed for expression of SRSF1 (Cotolog Number 32-46000) from Novex by Life Technologies (Carlsbad, Calif.) or T7-Tag (Catalog Number 69522) from EMD Millipore (Merck KGaA, Darmstadt, Germany). For detection of LacZ, MYC-tag antibody SC40 clone 9E10 (Catalog Number sc-40) from Santa Cruz Biotechnology (Dallas, Tex.) was used. For detection of p3x-FLAG-HNRNPD and FLAG-hnRNPD, ANTI-FLAG clone M2 (Catalog Number F1804) from Sigma-Aldrich (St. Louis, Mo.) was used. To detect expression of pFRT/TO/HIS/FLAG/HA-hnRNPR, anti-HA High Affinity (Catalog Number 11867423001) from Roche Diagnostics (Indianapolis, Ind.) was used. For detection of FLAG-GFP-hnRNPU, anti-GFP (Catalog Number ab13970) from Abcam (Cambridge, Mass.) was used. To detect expression of β-Actin clone AC-15 (Catalog Number A5441) from Sigma (St. Louis, Mo.) was used. For detection of β-tubulin expression, clone E7 was used from a hybridoma. Protein sizes were determined using the Precision Plus Protein Dual Color Standards marker (Catalog Number 161-0374) from Life Technologies (Carlsbard, Calif.).

RNA Oligonucleotide Pull Down

RNA probes were synthesized from Integrated DNA Technologies (Coralville, Iowa) (SRSF1-WT 'UAUCAG-GCAGGGGAGAGUGAU' (SEQ ID NO: 16) and SRSF1-MUT 'UAUCAGAAAGGGGAGAGUGAU' (SEQ ID NO: 17)). 5 nmol of RNA was modified and purified in a 400 µl reaction containing 100 mM NaCH3COO—, 5 mM NaIO4, pH 5.0 for 1 hour in dark. RNA was ethanol precipitated and resuspended in 50 µl 0.1 M NaCH3COO—, pH 5.0. Adipic acid dihydrazide agarose beads (Catalog Number A0802-10ML) from Sigma (St. Louis, Mo.) were washed four times in 0.1 M NaCH3COO— and incubated with RNA overnight at 4° C. on rotator. Bead-conjugated was washed successively three times in 2 M NaCl, then Buffer D (20 mM HEPES-KOH, pH 8.0, 20% glycerol, 0.1 M KCl, 0.2 mM EDTA, 0.5 mM DTT) spinning 300 rpm, and resuspended in 62.5 µl Buffer D. RNA was then incubated in a splicing reaction at 30° C. for 40 minutes, gently mixing every 5 minutes. Protein-bound beads were washed three times in Buffer D, then eluted in 40 µl 2×SDS Buffer. Beads were boiled 100° C. for five minutes, then spun down 10000 rpm at 4° C. for 10 minutes. Eluates were collected and loaded in equal volume on 10% SDS-PAGE Gel, transferred to PVDF membrane and probed for SRSF1 (1:1000) and β-Actin (1:250000).

In Vitro Splicing

In vitro transcribed pre-mRNA using T7 MEGAscript (Catalog Number AM1334) by Ambion by Life Technologies (Carlsbad, Calif.) was obtained using PCR templates amplified from the various MDM2 or p53 minigenes and incorporating a T7 promoter region and a flag tag region at the 5' end. The primers utilized were to amplify PCR products for use as templates for the in vitro transcription were as follows: for the MDM2 3-11-12s and the MDM2-based chimeric minigenes: For: 5'5' AGTAATACGACT-CACTATAGGGATTACAAGGATGACGACGA-TAAGAGCCCG GGCGGATCCCCACCTCACAGATTC 3' (SEQ ID NO: 18) and Rev: 5' ACTTACGGC-CCAACATCTGTTGCAATGTGATGG3' (SEQ ID NO: 19) with a 5' splice site and the primers for the p53 7-8-9 minigene and the p53-based chimeric minigenes were as follows: For: 5' AGTAATACGACTCACTATAGGGATTA-CAAGGATGACGACGATAAGGTTGGCTCT GACTG-TACCACCATC 3' (SEQ ID NO: 20) and Rev: 5' ACT-TACGGCTGAAGGGTGAAATATTCTCCATCC 3' (SEQ ID NO: 21) with a 5'ss at the end. 20 fmol of the MDM2 and p53 minigene in vitro transcribed RNA was subjected to in vitro splicing at 30° C. in nuclear extracts from normal or 12-hour cisplatinum-damaged HeLa S3 cells as previously described. Singh et al., 2009. RNA was extracted by standard phenol/choloroform and precipitated with 100% ethanol. RNA was reverse transcribed and subjected to a 25-cycle PCR as indicated above. PCR products were loaded on a 6% denaturing urea-PAGE gel, dried at 80° C. for 45 minutes and exposed to a phosphor screen overnight. The marker used was the radioactively-labeled, in vitro transcribed RNA century marker (Catalog Number AM7140) from Life Technologies (Carlsbad, Calif.). The sequences for the gene-specific primers (for the MDM2 and p53 minigenes and their corresponding chimeric minigenes) and the Flag-tag primer used have been described in Singh et al., 2009.

Ribooligonucleotide Competition

Splicing reactions with nuclear extracts from 12-hour cisplatinum-damaged HeLa S3 cells were pre-incubated at 30° C. in the presence of absence of 200 pmol oligonucleotides (SRSF1-WT 'UAUCAGGCAGGGGAGAGUGAU' (SEQ ID NO: 22) or SRSF1-MUT 'UAUCA-GAAAGGGGAGAGUGAU' (SEQ ID NO: 23)) for one hour. At one hour 20 fmol of the MDM2 3-11-12s minigene was added to each reaction and spliced as previously described for 2 hours. Singh et al., 2009.

Quantification of Splicing Ratios

Percentages of full-length and skipped products were quantitated using ImageQuant TL (Version 8.1). Results were plotted in FIGS. 1-5, SEM was used, and the significance of the results was assessed using the two-tailed Student's t-test using GraphPad Prism (Version 6.0).

Cell Culture, Growth, and Transfection Conditions

HeLa and MCF-7 cell lines were maintained in Dulbecco's modified Eagle's medium (DMEM) supplemented with 10% fetal bovine serum (Catalog Number SH3007103) from Thermo Fisher Scientific (Hudson, N.H.), L-glutamine (Catalog Number MT 25-005 CI) from Corning (Tewksbury, Mass.), and penicillin/streptomycin (Catalog Number MT 30-001 CI) by Corning (Tewksbury, Mass.). For transfection of MDM2 minigenes along with SRSF1 or LacZ overexpression plasmids, cells were seeded to 60% confluency and transfected with either with 0.5 μg of the MDM2 3-11-12s wild-type minigene and 4.5 μg of SRSF1 or LacZ (FIG. 5 D-F experiment), or 2.5 μg MDM2 3-11-12s wild-type or 174, 175 mutant minigenes and 2.5 μg of SRSF1 or LacZ (FIG. 5A-C experiment) using X-tremeGENE 9 (Catalog Number 06365779001) from Roche (Mannheim, Germany) according to the manufacturer's protocol. For transfection of oligonucleotides (e.g., antisense oligonucleotides r ASOs), MCF-7 cells were seeded to 60% confluency and transfected with Lipofectamine LTX (Catalog 15338-100) from Life Technologies (Carlsbad, Calif.) according to the manufacturer's protocol. For damage treatment, cells were split into treatment groups (normal, UV, cisplatinum) 18 hours after transfection and treated at 24 hours with 50 J/m2 UV or 75 μM cisplatinum for 24 hours, then harvested for RNA using an RNeasy kit (Catalog 74106) from Qiagen (Valencia, Calif.) and subjected to RT-PCR using conditions described above; 1 mg/ml stock of cisplatinum (manufactured for Teva Parenteral Medicine Inc., Irvine, Calif., and obtained from the Nationwide Children's Hospital pharmacy) in sodium chloride solution (pH 3.2-4.4) was used for cisplatinum treatment of cells.

SRSF1 Knockdown

Depletion of SRSF1 was performed using double-stranded siRNAs. The siRNAs targeting human SRSF1 (SRSF1 3'UTR-siRNA sense, UUGGCAGUAUUGAC-CUUAUU (SEQ ID NO 24); SRSF1 3'UTR-siRNA antisense, UAGGUCAAUACUGCCAAUU (SEQ ID NO: 25)) or a non-specific siRNA (CTRL sense, AAGGUCCGG-CUCCCCCAAAUG (SEQ ID NO: 26); CTRL antisense, CAUUUGGGGGAGCCGGACCUU (SEQ ID NO: 27)) were synthesized by Life Technologies (Carlsbad, Calif.). siRNAs were transfected into MCF-7 cells at a final concentration of 30 nM, mediated by Lipofectamine RNAiMAX from Life Technologies (Carlsbad, Calif.) for a total of 72 hours. At 40 hours post-transfection cells were split into normal and UV treatment groups and at 48 hours were either treated under normal conditions or exposed to 50 J/m2 UVC. 72 hours post-transfection cells were harvested for total RNA using an RNeasy kit (Catalog 74106) from Qiagen (Valencia, Calif.) and subject to RT-PCR as described above. Protein was also collected as described above to confirm knockdown of SRSF1.

Oligonucleotide Treatment

2'O-methyl antisense oligonucleotides were generated from Trilink. SRSF1-specific OLIGOs (#1 'GUAUCAG-GCAGGGGAGAGUG' (SEQ ID NO: 6), #2 'CAGGCA-GGGGAGAGUGAUAC' (SEQ ID NO: 7)) or a non-specific ASO 'AUAUAGCGACAGCAUCUUCC' (SEQ ID NO: 28)) were transfected into MCF-7 using Lipofectamine LTX (Catalog 15338-100) from Life Technologies (Carlsbad, Calif.) according to the manufacturer's protocol. At 18 hours post-transfection cells were split into normal and UV treatment groups and at 24 hours were either treated under normal conditions or exposed to 50 J/m2 UVC. 24 hours post-treatment cells were harvested for total RNA using an RNeasy kit (Catalog 74106) from Qiagen (Valencia, Calif.) and subject to RT-PCR as described above.

Results

Minimalized MDM2 Minigene 3-11-12s is Responsive to Stress In Vitro.

The inventors have previously shown that MDM2 minigenes recapitulate the damage-responsive splicing of the endogenous MDM2 pre-mRNA and thus can be utilized to understand the mechanisms regulating this splicing event. Jeyaraj et al., Front Biosci (Landmark Ed), 14, 2647-2656 (2009). The previously published damage-responsive minigene 3-11-12 (Singh et al., Exp Cell Res, 315, 3419-3432

(2009)) was used to closely map the cis elements that are involved in the regulated splicing of MDM2. A minimal stress-responsive MDM2 minigene called the 3-11-12s minigene was engineered, comprising exons 3, 11 and 12 and conserved flanking intronic regions to contain minimal sequences in the introns and the terminal exons retaining the core splicing signals. Specifically, the 3-11-12s minigene was created by truncating exons 3 and 12 of the 3-11-12 minigene to retain only 38 nt and 73 nt at their 3' and 5' ends respectively. The upstream chimeric intron (I3/10) of the 3-11-12 minigene was truncated to 72 nt (from 167 nt) and the downstream intron 11 to 147 nt (from 316 nt) in the 3-11-12s minigene. Importantly, the internal exon 11 remained intact, so splicing regulation could be thoroughly assessed. The 3-11-12s minigene, like its parent minigene, is responsive to genotoxic stress in vitro (FIG. 1A) and in cellulo (FIG. 4) and excludes internal exon 11 specifically under stress (9.4%±4.6% SEM 3.12 product under normal conditions versus 76.2%±6.0% SEM under damage conditions), indicating that the minimal sequences included in the 3-11-12s minigene are sufficient to recapitulate the stress-induced alternative splicing of MDM2. Importantly, the difference in the levels of 3.12 product between normal and cisplatinum-treated conditions was statistically significant (Student's t-test, p=0.0009).

Exon 11 of the MDM2 3-11-12s Minigene is Necessary for its Genotoxic Stress-Response.

To narrow down the cis elements that are important for mediating the stress-responsive alternative splicing of the MDM2 3-11-12s minigene, an intron-exon swap approach was employed between the stress-responsive MDM2 3-11-12s minigene (FIG. 1A) and a non-responsive p53 7-8-9 minigene (FIG. 1B) (36). Briefly, chimeric minigenes were generated by interchanging the introns and/or the internal exon of the MDM2 minigene with corresponding regions from the p53 minigene. In all cases, the 5' and 3' splice sites that are native to the exonic elements were retained (10 nucleotides of the intronic elements flanking the exon and bearing the respective splice sites). These chimeric minigenes were then subjected to in vitro splicing in nuclear extracts prepared from untreated or cisplatinum-treated Hela S3 cells and the spliced products were visualized using an RT-PCR approach as described previously. Singh et al., 2009. The ratio of the skipped product (3.12) to the corresponding full-length spliced product (3.11.12 for the MDM2 minigene or 3.8.12 for the chimeric minigenes containing the p53 exon) was determined using the ImageQuant software (Version 8.1) and the percent 3.12 product under each condition is represented graphically and assessed for statistically significant differences between normal and damaged splicing conditions.

When both the introns and exon 11 of the MDM2 minigene were replaced with introns 7 and 8 and exon 8 of the p53 minigene, the chimeric MDM2 minigene lost the ability to splice differentially and generated predominantly the exon 11 skipped product (3.12) in both extracts from normal and cisplatinum-treated cells. The splicing of this minigene resulted in the generation of 66.9% (±6.4% SEM) 3.12 product even in nuclear extracts from normal cells (FIG. 2A) as opposed to the basal level of 9.4% (±4.6% SEM) 3.12 product in the wild-type MDM2 3-11-12s minigene (observed in three independent experiments; compare FIG. 2A to FIG. 1A). However, in nuclear extracts from cisplatinum-treated cells the splicing of the chimeric minigene was comparable to the stress-induced splicing of the wild-type MDM2 minigene and generated 78.9% (±7.4% SEM) of the 3.12 skipped product across three separate trials (compare FIG. 2A to FIG. 1A). Moreover, the difference in the percent 3.12 splicing of the chimeric minigene between normal and cisplatinum-damaged conditions was not statistically significant (Student's t-test p=0.2883, FIG. 2A), unlike the wild-type MDM2 3-11-12s minigene. This indicates that the elements contained within the introns and/or the internal exon 11 of the MDM2 3-11-12s minigene are necessary for the damage-specific response and their loss resulted in the formation of a steady expression of this 3.12 product even under normal conditions (FIGS. 2A, F).

Next, either the upstream (I3/10) (FIG. 2B) or downstream (I11) (FIG. 2C) or both introns (FIG. 2D) were removed from the MDM2 minigene and replaced them with the corresponding introns from the non-responsive p53 minigene (5' and 3' splice sites in these constructs were those native to the exons of the respective minigene, and not from the introns being inserted). These chimeric MDM2 minigenes retained the damage response and showed statistically significant increase in percent 3.12 skipped product in nuclear extract from cisplatinum damaged cells (an average of 67.5% for all three chimeric minigenes in three separate experiments) compared to the nuclear extract from normal cells (an average of 32.1%; FIGS. 2B, C, D, F). This behavior was comparable to the damage-responsive splicing of the wild-type MDM2 3-11-12s minigene, although there was a slight increase in the baseline percent skipped 3.12 product in the normal nuclear extract (compare FIG. 1A to FIGS. 2B, C, D, F). However, when exon 11 of the MDM2 minigene was removed and replaced with exon 8 of the p53 minigene, the chimeric MDM2 minigene failed to show the damage-responsive splicing ratio change (FIGS. 2E, F). Indeed, the percent 3.12 skipped product obtained when this minigene was spliced in nuclear extracts from normal cells (16.9±11.2% SEM) and the percent 3.12 obtained from splicing in nuclear extracts from cisplatinum-damaged cells (17.9±2.8% SEM) were not significantly different (Student's t-test, p=0.9344). Together, these data indicate that exon 11 of the MDM2 minigene contains important elements that regulate the damage responsive alternative splicing of the MDM2 minigene.

Exon 11 of the MDM2 3-11-12s minigene is necessary and sufficient to sustain genotoxic stress-response in a heterologous context.

Figures 3A, 3B, 3C, 3D:
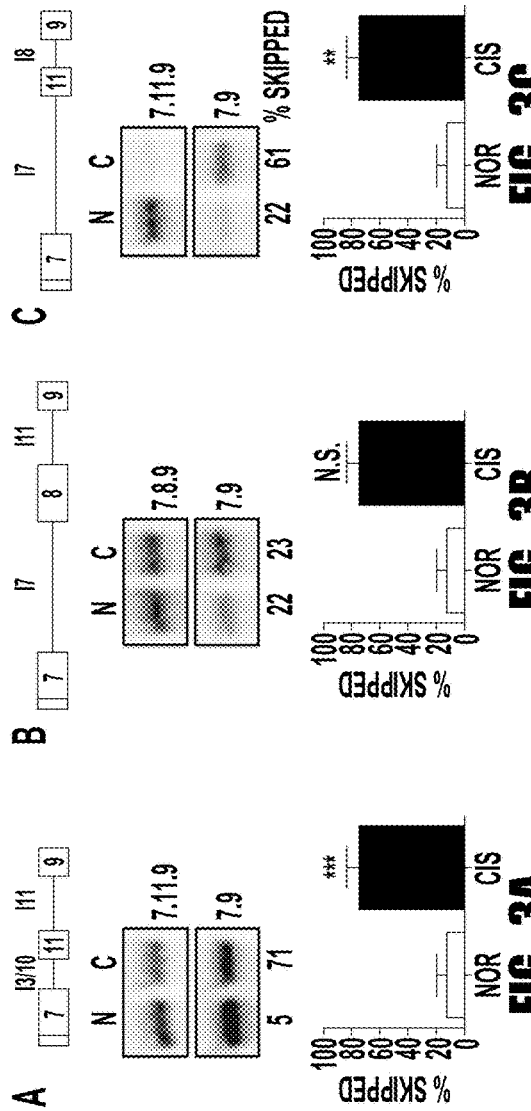
FIGS. 3A-3D provide graphs and images showing the MDM2 exon 11 is sufficient to regulate stress-responsive splicing in the heterologous p53 minigene context. Chimeric p53 minigenes were created by replacing the introns and/or internal exon of p53 with corresponding regions from the stress-responsive MDM2 minigene. These minigenes were then spliced in vitro in nuclear extracts prepared from normal (N) and cisplatinum (C) treated cells. Percentage of the skipped splicing product 7.9 for the various chimeric minigenes is represented graphically for three independent experiments and the error bars reflect the standard error mean (SEM). (a) The chimeric construct in which the p53 minigene's internal exon 8 and its flanking introns were replaced by the corresponding regions of the MDM2 3-11-12s minigene exhibited damage-specific skipping of the internal exon in a manner similar to the wild-type MDM2 3-11-12s minigene. The difference in the percentage of the 7.9 skipped product generated between normal and cisplatinum-damaged conditions was statistically significant (n=3). (b) The chimeric p53 minigene in which its downstream intron 8 was replaced by intron 11 of the MDM2 3-11-12s minigene did not show statistically significant changes in the percentage of 7.9 product obtained as a result of splicing under normal and cisplatinum-damaged conditions (n=3). (c) The in vitro splicing of the chimeric p53 minigene containing the exon 11 of MDM2 minigene in nuclear extracts from normal and cisplatinum-treated cells showed statistically significant damage-specific induction of the 7.9 skipped product in a manner similar to the wild-type MDM2 3-11-12s minigene (n=3). (d) Table summarizing the p53 minigene constructs and the status of their damage-responsive splicing. Splicing status of (−) indicates that constructs were not splicing competent in nuclear extracts as fully-spliced products were not detected by RT-PCR.

Reciprocal chimeras of the p53 minigene were then constructed, which normally does not show splicing changes in response to stress (36.1±4.8% SEM under normal or 40.1±3.4% SEM under cisplatinum-damaged conditions of the 7.9 skipped product; FIG. 1B). For these constructs, native elements of the p53 minigene were replaced with the corresponding intronic or exonic elements of the MDM2 minigene. When exon 8 of the p53 minigene and its flanking introns were replaced with both flanking introns and exon 11 of the MDM2 minigene, the chimeric p53 minigene exhibited damage-responsive alternative splicing similar to the wild-type MDM2 minigene (percent 7.9 spliced product was 12.6±4.2% SEM under normal and 75.1±5.5% SEM under cisplatinum-damaged conditions, p=0.0008 with Student's t-test) (FIGS. 3A, D). This indicates that the cis elements contained within the MDM2 minigene's internal exon and introns are sufficient to facilitate damage-specific alternative splicing in the heterologous p53 minigene system. The chimeras in which intron 7 of the p53 minigene was removed either by itself or in conjunction with the downstream intron 8, failed to splice at all in nuclear extracts from both normal and damage-treated cells as only the unspliced minigene transcripts were detected after RT-PCR (FIG. 3D). When intron 8 of the p53 minigene was replaced with intron 11 of the MDM2 minigene, there was a modest increase in the skipped 7.9 product in response to damage (40.7±8.9% SEM under cisplatinum-damaged compared to 25.1±2.5% SEM under normal conditions) although this change was not statistically significant (Student's t-test p=0.1694) (FIG. 3B, D). Strikingly, when exon 11 of the MDM2 minigene was inserted in the p53 minigene (MDM2 exon 11 was placed in the heterologous p53 minigene with its own exon 11 5' and 3' splice sites native to MDM2) in the place of the native p53 exon 8, the chimeric minigene responded to cisplatinum damage unlike the wild-type p53 minigene when spliced in nuclear extracts from stressed cells. Indeed, the percentage of the 7.9 skipped product increased from 32.7% (±5.4% SEM) in nuclear extract from normal cells to 71.1% (±5.9% SEM) in nuclear extracts from cisplatinum-treated cells (FIG. 3C, D) and this difference was found to be statistically significant (Student's t-test, p=0.0084). In short, the chimeric 7-11-9 p53 minigene behaved like the wild-type MDM2 3-11-12s minigene in response to damage indicating that MDM2 exon 11 is sufficient to confer damage response in a heterologous minigene context.

SRSF1 is a negative regulator of MDM2 alternative splicing.

To identify splicing factors that may be responsible for the damage-responsive alternative splicing of the MDM2 minigene, bioinformatics analysis of exonic splicing enhancers present in exon 11 was performed. Using a SELEX-based (systematic evolution of ligands by exponential enrichment) program called ESEfinder 3.0, which takes consensus-binding motifs for SR proteins derived from selective enrichment of 20-nucleotide random sequences for the splicing of a minigene in S100 extract supplemented with individual SR proteins, the sequence of the MDM2 minigene was entered to examine predicted binding sites for SR proteins. Smith et al., Hum Mol Genet, 15, 2490-2508 (2006); Cartegni et al., Nucleic Acids Res, 31, 3568-3571 (2003). Among the top hits was a site in MDM2 exon 3 and an overlapping pair of SRSF1 binding sites in exon 11, which were all conserved between mouse and human MDM2. The inventors then performed point mutations in our MDM2 minigene to disrupt the binding affinity of SRSF1 for its predicted sites. Importantly, precise mutations were made that maintained other binding sites for overlapping bioinformatically-predicted factors SRSF2 (SC35), SRSF5 (SRp40), and SRSF6 (SRp55). In the case of the pair of SRSF1 binding sites in exon 11, a single mutation was not sufficient to disrupt both SRSF1 binding sites, so a double mutant, SRSF1-174, 175, was created. The strength of each splicing enhancer site corresponds to a scale in which a higher numeric matrix score indicates greater predicted binding strength. The mutations made in SRSF1-48 and SRSF1-174, 175 significantly lowered the predicted ESE value from 3.05 to 0.74 and 3.23 to 1.37, respectively. Site-directed mutagenesis of these sites was then performed on the MDM2 minigene to assess the effects of these mutations on splicing.

Figure 4A:
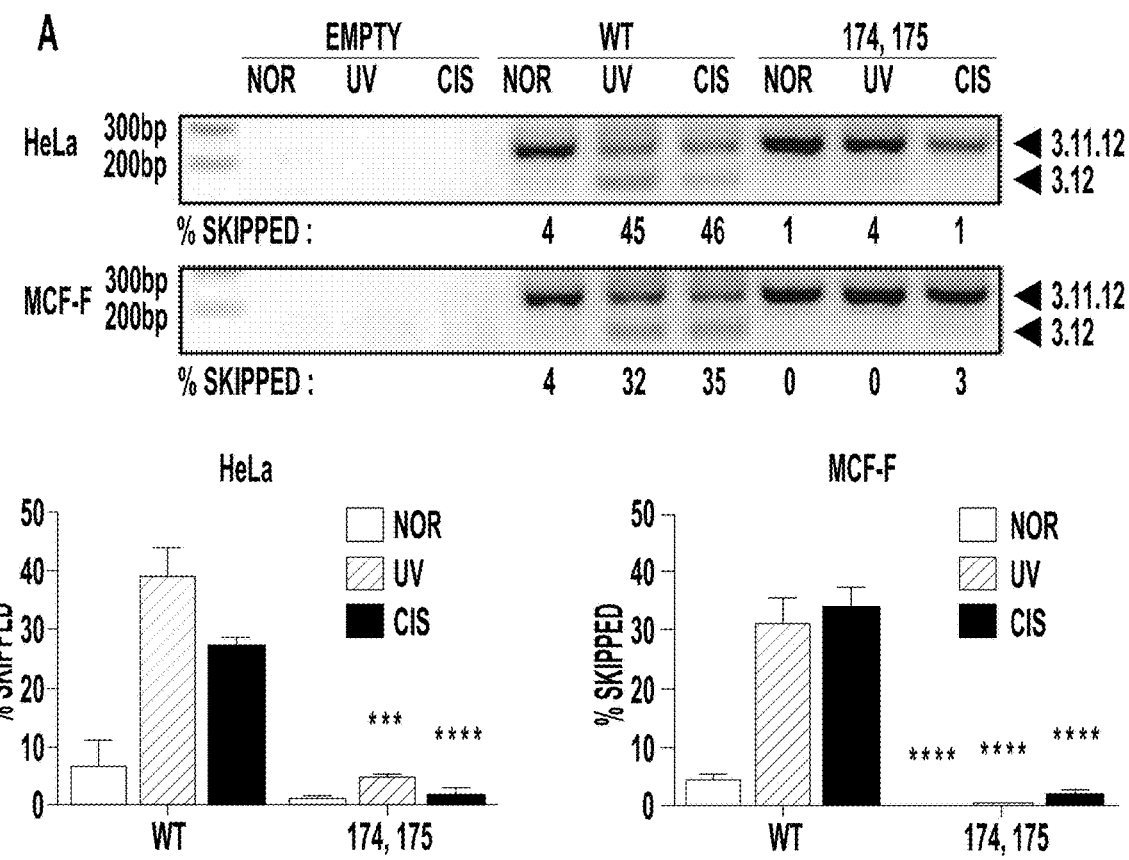
FIGS. 4A and 4B provide graphs and images showing SRSF1 acts a negative regulator of splicing in MDM2 exon 11. MDM2 minigenes were transfected into MCF-7 and HeLa cells for 24 hours and then treated under normal, 50 J/m$^2$ ultra-violet (UVC) or 75 μM cisplatinum (CIS)-damaged conditions for an additional 24 hours. RNA was extracted and subjected to RT-PCR using a minigene and gene-specific primer. PCR products were separated on a 1.5% agarose gel and spliced products were visualized by UV imaging. The bar graphs represent the percentage of 3.12 skipped product obtained from three independent experiments under each condition and the error bars represent standard error mean (SEM). The SRSF1 mutant minigene loses damage-induced alternative splicing (MCF-7 n=4, HeLa n=3).
Figure 4B:
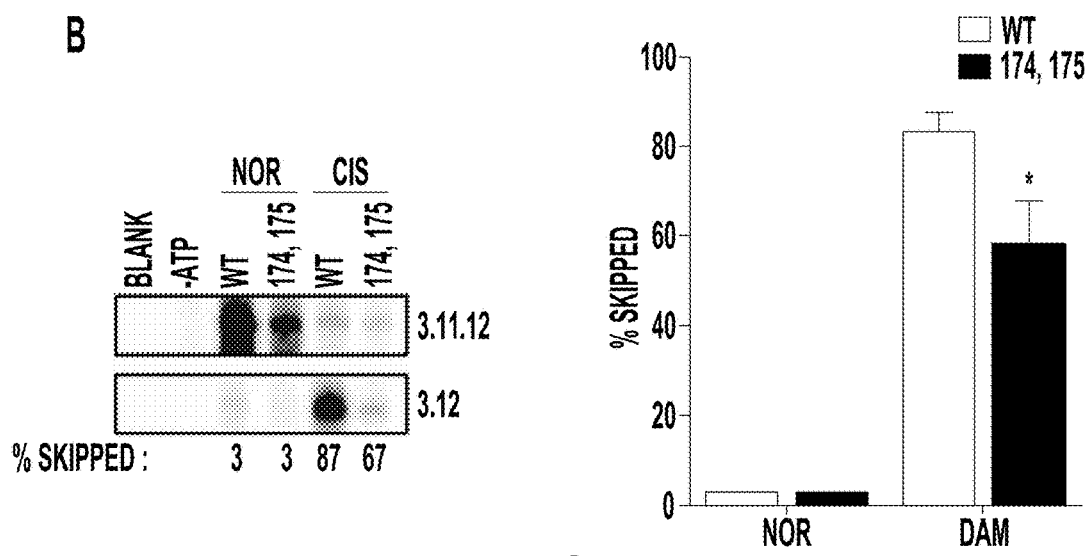

The splicing of the wild-type and SRSF1 mutant MDM2 minigenes was examined in vivo in HeLa and MCF-7 cells. These cell lines were chosen for their relative ease of transfection and ability to tolerate genotoxic stress. The splicing patterns of the wild-type and the SRSF1 mutant minigenes were compared under the different conditions. Although the mutation at the SRSF1-48 site was predicted to disrupt the ESE in exon 3 (the matrix score was lowered for SRSF1-48), it was observed that the corresponding mutant minigene (15.890%±5.683 SEM NOR, 49.220%±1.265 SEM UV) did not show altered splicing compared to wild-type (19.050%±6.466 NOR, ±48.630%±1.860 UV) under both the normal (p=0.7317) and UV-treated conditions (p=0.8049). However, mutation of the SRSF1 sites in MDM2 exon 11 (174,175 mutant minigene) eliminated the damage-responsive exon 11 skipping upon UV (MCF-7 0.270%±0.01958 SEM, HeLa 4.933%±0.3093 SEM) and cisplatinum treatment (MCF-7 2.235%±0.4246 SEM, HeLa 1.800%±0.6848 SEM) compared to the skipping of the wild-type minigene under UV and (MCF-7 31.200%±2.140 SEM, HeLa 39.227%±2.819 SEM) cisplatinum (MCF-7 33.935% CIS±1.709 SEM, HeLa 27.330%±0.7490 SEM) treatments (FIG. 4). The decrease in exon 11 skipping observed in the SRSF1 174,175 mutant minigene under normal and damaged conditions was statistically significant when compared to the wild-type minigene (Student's t-test p<0.0001).

SRSF1 overexpression induces exclusion of MDM2 exon 11.

Figure 5A:
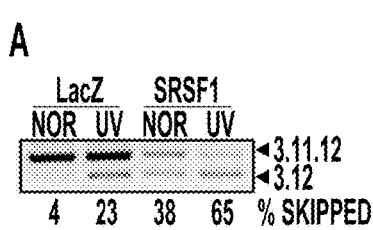
FIGS. 5A-5I provide graphs and images showing SRSF1 induces exclusion of MDM2 exon 11. (A) LacZ or T7-SRSF1 were cotransfected with the MDM2 3-11-12s minigene in MCF-7 cells for 24 h and then treated under normal or 50 J/m2 ultra-violet (UVC) conditions for an additional 24 h. RNA was extracted and subjected to a RT-PCR using a minigene- and gene-specific primer. PCR products were separated on a 1.5% agarose gel and spliced products were visualized by UV imaging (n=3). (B) The bar graphs represent the percentage of 3.12 skipped product obtained from three independent experiments under each condition and the error bars represent SEM. Overexpression of T7-SRSF1 in transfected MCF-7 cells under both normal and UV conditions induced skipping of exon 11 in the WT MDM2 3-11-12s minigene compared to the negative control (LacZ). (C) Protein lysates were run on a 10% SDS-PAGE gel and probed with C-MYC, T7 and β-Actin antibodies to confirm protein overexpression. (D) The MDM2 minigenes (WT or MUT) and LacZ or T7-SRSF1 were cotransfected in MCF-7 cells for 24 h. RNA was extracted and subjected to a radioactive RT-PCR using a minigene- and gene-specific primer. PCR products were separated on a 6% Urea-PAGE gel and spliced products were visualized by autoradiography (n=3). (E) Overexpression of T7-SRSF1 in transfected MCF-7 cells under normal conditions induced skipping of exon 11 in the WT minigene compared to the negative control (LacZ), whereas the SRSF1 mutant was unresponsive to damage induction. Representative data of triplicate experiments is shown. (F) Protein lysates were run on a 10% SDS-PAGE gel and probed with C-MYC, T7 and β-Actin antibodies to confirm protein overexpression. (G) MCF-7 cells were transfected with either 30 nM of non-specific (CTRL) or SRSF1-specific (SRSF1). At 42 h, cells were split 1:2 and at 48 h were cultured either normally or treated with 50 J/m2 ultra-violet (UVC) for 24 h. At 72 h post-transfection, cells were harvested for RNA and protein. RNA was reverse transcribed and subjected to a nested PCR. PCR products were separated on a 1.5% agarose gel and spliced products were visualized by UV imaging. The percent of MDM2-ALT1 is shown relative the amount of full-length MDM2 (MDM2-FL). The bar graph (H) represents the percentage of MDM2-ALT1 skipped product obtained from three independent experiments and the error bars represent SEM. Upon knockdown of SRSF1, endogenous MDM2 loses damage-inducible expression of MDM2-ALT1 (n=3). (I) Protein lysates were run on a 10% SDS-PAGE gel and probed with SRSF1 and β-Tubulin antibodies to confirm protein knockdown.
Figure 5B:
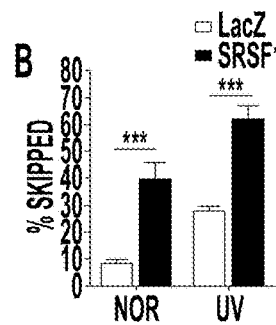
Figure 5C:
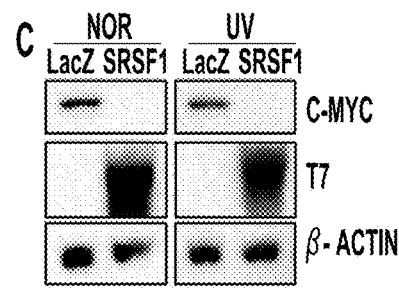
Figure 5D:
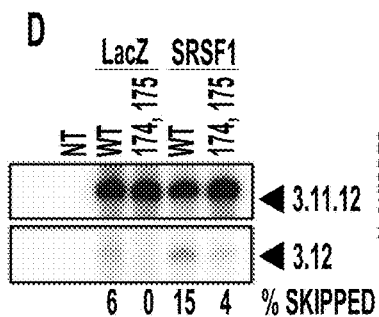
Figure 5E:
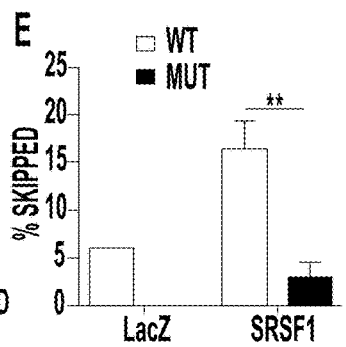
Figure 5F:
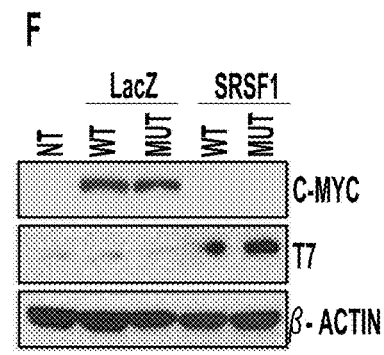

To determine whether SRSF1 acts as a regulator of MDM2 alternative splicing, a T7-tagged SRSF1 construct or a negative control, LacZ and the wild-type 3-11-12s minigene was overexpressed in MCF-7 cells. Compared to LacZ (8.487%±1.149 SEM), SRSF1 overexpression (39.700%±6.322 SEM) significantly (p=0.0007) induced skipping of exon 11 in the wild-type minigene even in the absence of genotoxic stress (FIGS. 5A-C). Similarly under UV damaged conditions, overexpression of SRSF1 induced higher levels of 3.12 skipped product (62.020%±5.016 SEM) compared to LacZ overexpression (28.020%±1.722 SEM) (p=0.0002) (FIGS. 5A-C). A similar experiment was performed using the 3-11-12s mutant minigene, for which the SRSF-1 174, 175 sites are mutated. The ability of SRSF1 overexpression to induce exclusion of exon 11 was reduced (3.550%±0.8709 SEM) when coexpressed with the SRSF1-174, 175 mutant minigene when compared to the wild-type minigene (16.390%±1.675 SEM) (FIGS. 5D-F). Overexpression of MYC-LacZ and T7-SRSF1 were confirmed by immunoblotting (FIG. 5C, FIG. 5F). These results suggest a negative role for SRSF1 in the regulation of MDM2 splicing.

To confirm that the effect of SRSF1 was not a non-specific effect due to the protein's ability to bind RNA, additional RNA binding proteins were tested whose binding was not predicted using ESEfinder 3.0. To this end, a panel of hnRNPs (D, F, L, R and U) was overexpressed in MCF-7 cells and assessed their function on the splicing of the MDM2 3-11-12s minigene under normal and UV-treated conditions. It was observed that the splicing patterns of the MDM2 3-11-12s minigene did not show any significant differences between LacZ and hnRNP overexpression under both normal and damaged conditions. Overexpression of LacZ and the individual hnRNPs was confirmed by immunoblotting.

SRSF1 knockdown rescues damage-induced skipping of MDM2.

Figure 5G:
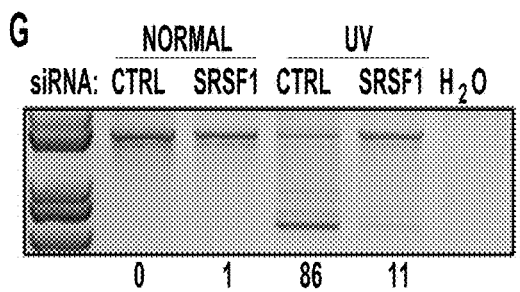
Figure 5I:
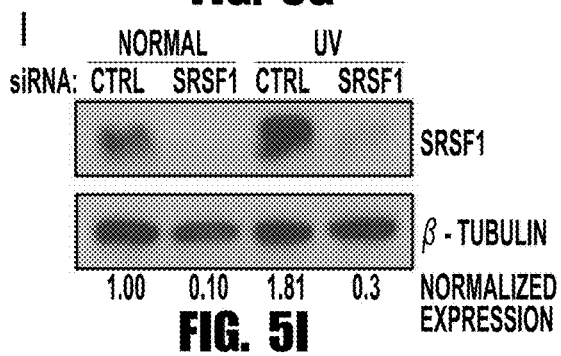
Figure 5H:
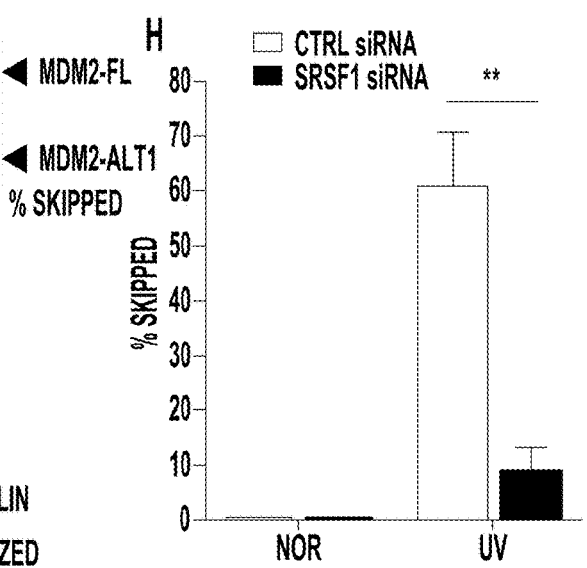

Next, the effects of SRSF1 knockdown on the ability of genotoxic stress to induce MDM2-ALT1 were examined. To this end, MCF-7 cells were transfected with a non-specific (CTRL) or SRSF1-specific siRNA (SRSF1). siRNA-mediated knockdown of SRSF1 resulted in approximately six-fold decrease (p=0.0082) in the percentage of MDM2-ALT1 (endogenous 3.12 skipped product) induced under UV treatment (9.297%±4.159 SEM) when compared to non-specific siRNA-transfected cells (60.950%±9.757 SEM) (FIGS. 5G and 5H). The inventors confirmed efficient knockdown (85-95%) of SRSF1 by immunoblotting (FIG. 5I). Taken together, these data further support SRSF1 as a negative regulator of MDM2 alternative splicing.

An increase in relative SRSF1 protein levels as observed under UV treatment (FIG. 5F, Lane 3) compared to normal conditions (FIG. 5F, Lane 1). To investigate the UV-induced upregulation of SRSF1, its transcript levels was examined at several time points over 24 hours of UV irradiation using qRT-PCR. As a positive control, the levels p53-responsive CDKN1A (that encodes cell-cycle regulator p21) were examined, whose expression is upregulated at both transcript and protein levels under conditions of genotoxic stress. Macleod, Genes Dev, 9, 935-944 (1995). As expected, CDKN1A transcript levels increased upon UV treatment. However in the case of SRSF1, an increase in transcript levels was not observed. Rather, a decrease in SRSF1 transcripts was observed over the course of 24 hours of UV treatment, a phenomenon that is consistent with a general inhibition of RNA synthesis under DNA damaging conditions. Rockx et al., Proc Natl Acad Sci USA, 97, 10503-10508 (2000). However, another means of regulating SRSF1 levels is via its alternative splicing in the 3'UTR and six major splice variants have been characterized of which only isoforms I and II can generate full-length protein. Sun et al., Nat Struct Mol Biol, 17, 306-312 (2010). When the relative levels of the various splice forms of SRSF1 between normal and DNA damage conditions were examined, a significant increase (p=0.0005) in the levels of the productive isoforms I and II under UV treatment (64.667% isoform I/II±2.028 SEM) was observed as compared to normal treatment (36.333% isoform I/II±1.856 SEM) with a concomitant decrease in expression of isoforms III to VI. This raises the possibility that upregulation of the productive splice forms I and II under UV contributes to the observed increase in SRSF1 levels.

SRSF1 binds exonic splicing enhancer elements in MDM2 exon 11.

To determine whether SRSF1 acts a regulator of MDM2 alternative splicing via direct binding to exon 11, in vitro binding studies were performed. Both wild-type and mutant oligonucleotides were synthesized encompassing the binding site in exon 11, and their ability to bind or pull down SRSF1 in splicing-competent nuclear extracts was tested (FIG. 6A). An in vitro RNA oligonucleotide pull down was performed using wild-type and mutant oligonucleotides in nuclear extracts from both normal and cisplatinum-treated HeLa S3 cells. SRSF1 showed increased binding to the wild-type oligonucleotide under cisplatinum-damaged conditions as compared to normal conditions (FIG. 6B, Lane 5, 7), consistent with the increased levels of SRSF1 in the cisplatinum-treated nuclear extract (FIG. 6B, Lane 1, 2). Importantly, SRSF1 showed decreased binding to the mutant oligonucleotide both under normal and cisplatinum-damaged conditions (FIG. 6B, Lanes 6 & 8) indicating that mutation of these sites in exon 11 attenuates SRSF1 binding. Furthermore, the inventors observed that a molar excess of the wild-type exon 11 oligonucleotide, but not the 174,175 mutant was able to successfully compete with and alter the splicing of the wild-type MDM2 3-11-12s minigene in nuclear extracts from cisplatinum-treated Hela S3 cells (compare percent 3.12 skipped product in the absence of competing oligonucleotides [99.940%±0.023 SEM] and in the presence of wild-type [88.160%±1.455 SEM, (p=0.0002)] or mutant [95.720%±3.282 MUT (p=0.1852)] oligo, FIGS. 6C, 6D). Taken together these results indicate that SRSF1 binds MDM2 exon 11 at the 174,175 site and regulates the damage-induced alternative splicing. Mutations at this site that inhibit SRSF1 binding also abrogate the stress-specific exclusion of exon 11.

Oligonucleotides (OLIGOs) modulate endogenous MDM2 alternative splicing under genotoxic stress.

To investigate the importance of the SRSF1 binding elements in MDM2 exon 11 in the regulation of endogenous MDM2 splicing, we designed 2'O-methyl oligonucleotides targeting this region. We predicted that binding of the SRSF1 to the exon 11 SRSF1 sites in the oligonucleotide would occlude binding of the SRSF1 protein (FIG. 7A). To test this, we transfected MCF7 cells with exon 11 SRSF1 oligonucleotides (OLIGO1 and OLIGO2) and a non-specific control (NS-OLIGO). At the highest doses (500 nM) both OLIGO1 (10.480%±8.503 OLIGO) and OLIGO2 (9.253%±8.772 OLIGO2) containing the SRSF1 sites in exon 11 ablated the formation of endogenous MDM2-ALT1 under UV-damaged conditions (FIG. 7B) and this difference in induction was statistically significant (FIG. 7C, OLIGO1 p=0.0322 and OLIGO2 p=0.0307). However, the non-specific OLIGO (NS) had no effect and MDM2-ALT1 transcripts were induced under UV-treated conditions at all doses of the NS-OLIGO (FIG. 7B).

Figure 8:
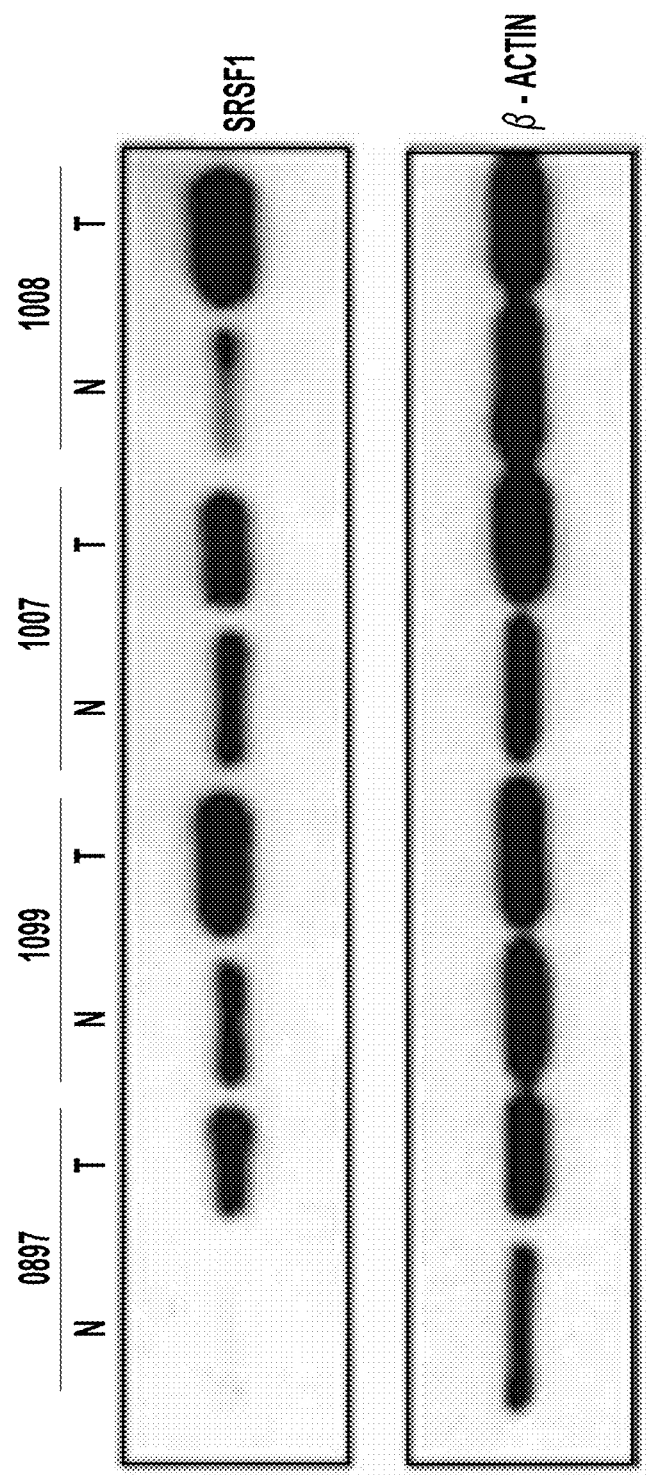
FIG. 8 provides a gel image showing that SRSF1 is upregulated in rhabdomyosarcoma (RMS) tumor tissues. Frozen rhabdomyosarcoma patient samples and normal tissue-matched control were homogenized and extracted for protein. Protein lysates were run on a 10% SDS-PAGE gel and probed with SRSF1 and β-Actin antibodies to confirm protein levels. SRSF1 is upregulated in tumor tissues of RMS patients compared to their normal tissue-matched controls. Normalized expression values for tumor (T) samples compared to normal muscle (N) are depicted below the graph.

SRSF1 is overexpressed in rhabdomyosarcoma patient samples:

MDM2-ALT1 expression is observed in several cancer types including breast (Hori et al., Pathology international, 50, 786-792 (2000)), colon (Yu et al., Cancer, 118, 1110-1118 (2012)), and glioblastoma (Kraus et al., Int J Cancer, 80, 930-934 (1999)). Additionally, the inventors have shown that MDM2-ALT1 is expressed in over 85% alveolar and 70% embryonal rhabdomyosarcoma (RMS) tumors and that its expression is correlated with high-grade metastatic disease, irrespective of histological subtype. Jacob et al., Neoplasia, 15, 1049-1063 (2013). To examine the relationship between the perturbed splicing of MDM2 and the expression of SRSF1, a panel of four RMS tumors that express MDM2-ALT1 constitutively and for which matched normal tissues were available was examined Elevated SRSF1 levels were observed in three of the four tumor samples compared to their corresponding normal tissue-matched controls (FIG. 8). Though the number of samples available with matched normal controls is small, the elevated SRSF1 expression in tumor samples correlates with the finding that overexpression of SRSF1 induces MDM2-ALT1.

Discussion

DNA damage-induced alternative splicing of MDM2 is observed in both human and mouse transcripts. Han et al., Mol Cell Biol, 31, 793-802 (2011) Additionally, both human and mouse Mdm2 possess conserved SR protein binding sites in their exon 11 suggesting that the alternative splicing of MDM2 could be an important, evolutionarily conserved mechanism for the titration of MDM2 levels under stress. Furthermore, functional studies have revealed a role for the stress-inducible splice forms of MDM2 in cancer underscoring the importance of this splicing event and the necessity to gain an understanding of the mechanisms involved in the damage-responsive splicing of MDM2. Using a novel damage-inducible in vitro splicing system the inventors have previously shown that intron 11 of MDM2 contains conserved positive elements that are primarily needed for the efficient full-length splicing of MDM2. Jacob et al., J Biol Chem, 289, 17350-17364 (2014) However, the factors governing its damage-responsive alternative splicing still remained to be elucidated.

In this example, the inventors used a minimal 3-11-12s minigene system to identify the cis splicing regulatory elements and the trans factors that directly mediate the damage-induced skipping of MDM2 exon 11. Using an intron-exon swap approach between the stress-responsive 3-11-12s and a non stress-responsive p53 minigene we demonstrate that exon 11 of MDM2 contains elements that are not only necessary, but also sufficient to regulate its damage-specific alternative splicing even in a heterologous p53 minigene context (FIGS. 1, 2 and 3). Moreover, this effect is independent of both the introns (upstream intron 3/10 and downstream intron 11) of the minimal 3-11-12s minigene (FIGS. 2 and 3). Interestingly, in a previous study the inventors observed that the splicing regulation of a larger version of the 3-11-12 MDM2 minigene containing additional positive acting elements in intron 11 (absent in the 3-11-12s minigene of the present study) was dependent upon intron 11. Singh et al., 2009. It is likely then that the shortened intron 11 of the minimal 3-11-12s minigene lacks the positive acting elements and also the counter-balancing negative elements thereby facilitating neutralization and eliminating the requirement for intronic regulatory elements. However, it should be noted that intron 11 irrespective of the MDM2 minigene that it was derived from, was insufficient to confer damage-responsive alternative splicing in the heterologous p53 minigene context (FIG. 3). Hence, in the context of endogenous MDM2 pre-mRNA it feasible to envision a scenario in which splicing regulation under normal and DNA damaged conditions is mediated by complex interactions between the intronic and exonic cis acting elements.

SRSF1-mediated splicing repression: In the present case, the inventors identify a conserved ESS element on exon 11 whose disruption results in the loss of exon 11 skipping in response to DNA damage. Furthermore, evidence is presented that SRSF1 binds this site and acts as a negative regulator of MDM2 splicing. Although canonically considered a splicing enhancer, SRSF1 has also been shown to act as a negative regulator of splicing in certain contexts. de Miguel et al., Cancer Res, 74, 1105-1115 (2014). Well known examples of SRSF1-mediated exon exclusion include the splicing of RONΔ11, a pro-oncogenic isoform of the Tyrosine kinase receptor RON and the exon 9 excluded form of CFTR. In the case of RON, the skipping of exon 11 is dependent on the binding of SRSF1 to ESE and ESS elements in the adjacent exon 12. Ghigna et al., Mol Cell, 20, 881-890 (2005). This generates RONΔ11 that promotes cellular invasion and motility. The best-characterized mechanism for SRSF1-mediated exon skipping is the binding of SRSF1 to a silencer motif in the intron downstream of CFTR exon 9 which allows the assembly of splicing machinery on a decoy exon thereby repressing the functional splicing signals in exon 9. Buratti et al., Nucleic Acids Res, 35, 4359-4368 (2007). However, the exact nature of this repression remains unclear.

Thus far, in the best-characterized examples of SRSF1-mediated splicing repression, this SR protein acts via intronic silencer elements (ISS) or enhancer elements located in the exons (ESE) flanking the regulated exon. Moreover, studies have shown that classical SR protein-binding ESE sequences, when inserted into intronic locations, can prevent splicing to the downstream 3'ss thus acting as repressors of splicing. Ibrahim et al., Proc Natl Acad Sci USA, 102, 5002-5007 (2005). In a converse scenario, when ISS elements bound by the SRSF10 (TRA2B) are relocated to an exon, they act as ESEs and favor exon inclusion. Shen, M. and Mattox, W., Nucleic Acids Res, 40, 428-437 (2012)

In the case of MDM2, this represents a unique instance wherein the damage-specific skipping of exon 11 is mediated by SRSF1 via a predicted exonic splicing enhancer (ESE) element located in the regulated exon itself. It is possible that the location of the element is responsible for directing the functionality of its SR protein binding partner. Indeed, position-dependent effects have been reported for the activity of exonic splicing regulatory elements that potentially shift the nature of the SR protein-mediated splicing regulation of alternative versus constitutive exons. Goren et al., Mol Cell, 22, 769-781 (2006). Additionally, complex evolutionary relationships exist between the exonic splicing regulatory elements (ESRs) and the alternatively spliced or regulated exons whose splicing they control. These involve strength of the 5' and 3' splice sites flanking regulated exons, conservation, location and abundance of the ESRs and various other factors that essentially blur the functional distinction between splicing enhancers and splicing silencer elements on alternatively spliced exons. These studies argue that SRSF1-mediated exon inclusion or exclusion relies on the contextual information of the surrounding exonic and intronic regions.

Moreover, transcriptome-wide analyses have correlated regulated exons with higher occurrence of ESS elements compared to constitutive exons that present with an abundance of ESE elements. Wang et al., Nucleic Acids Res, 33, 5053-5062 (2005). This is concordant with studies showing that majority of the alternative splicing in metazoans represents exon skipping events. Holste, D. and Ohler, U., PLoS computational biology, 4, e21 (2008). Taken together, these results suggest that exon 11 and potentially the other exons of MDM2 that are skipped in response to stress, harbor ESR elements whose location dictates ESS or ESE functionality and modulates the role of the trans protein factors binding them. However, more detailed computational analyses of the ESRs of MDM2 exons in relation to their splice site strengths, sequence conservation and trans factor binding site predictions coupled with experimental validation of the ESR functions are required to test this possibility.

Notably, SRSF1 binds the element on exon 11 both under normal and damaged conditions (FIG. 6). One possibility is that SRSF1 binding to exon 11 is non-functional in normal conditions and even serves to mask the ESS element. Another possibility is that SRSF1 binding to exon 11 under normal conditions serves as a splicing enhancer. However, the mutant MDM2 minigenes unable to bind SRSF1 do not show even baseline exon skipping under normal conditions indicating that this possibility may not be true (FIG. 4). Post-translational modifications including phosphorylation of SR proteins have been shown to modulate their catalytic activity (Zhong et al., Genes Dev, 23, 482-495 (2009)), suggesting that differential phosphorylation of SRSF1 could account for its activity under normal and damaged conditions. The inventors have found that this was also not the case because they observed no differences in the migration of SRSF1 between nuclear extracts from normal and cis-platinum-treated HeLa S3 cells that were either untreated or incubated with calf intestinal phosphatase (CIP).

What was observed was an increase in the levels of SRSF1 in nuclear extracts from cisplatinum-treated Hela S3 cells compared to nuclear extracts from normal cells. Concordantly, increased binding of SRSF1 to exon 11 under DNA damage compared to normal conditions was found (FIG. 6, Lane 7). Hence, the inventors propose a critical level of SRSF1 binding is necessary to cause repression of exon 11 splicing as seen under genotoxic stress. It is possible that under these conditions SRSF1 binding overrides the influence of other positive elements and trans factors and precludes the recognition of the flanking 5' and 3' splice sites and consequently the definition of exon 11 by the spliceosomal complex. Additionally, the differential binding of SRSF1 under DNA damage raises the intriguing possibility of crosstalk with other SR protein factors. For instance, the binding of other SR proteins and trans factors to ESRs adjacent to the SRSF1 site could cause their functional interaction with SRSF1 in a yin and yang fashion that mediates exon 11 inclusion under normal conditions and facilitates its exclusion in response to stress.

Impact on cancer: SRSF1 is located on chromosome 17 and is a commonly amplified region in breast cancer, correlating with poor prognosis. Sinclair et al., Breast Cancer Res Treat, 78, 313-322 (2003). SRSF1 regulates the alternative splicing of several tumor suppressor genes, kinases, and kinase receptors, all of which generate oncogenic isoforms. Furthermore Karni et al. have demonstrated that slight SRSF1 overexpression is capable of inducing cellular transformation in immortalized rodent fibroblasts in vitro as well as inducing sarcoma formation in nude mice. Karni et al., Nat Struct Mol Biol, 14, 185-193 (2007). As changes in alternative splicing have been shown to be important for the neoplastic phenotype, the global patterns of alternative splicing upon SRSF1 upregulation are important to understand. Recently, de Miguel et al. demonstrated that over 20 transcripts were regulated by SRSF1 in lung cancers. For example, siRNA-mediated knockdown of SRSF1 described herein prevented the inclusion of a lung carcinoma-associated exon in the transcript PRRC2C, and significantly reduced cell growth. de Miguel et al., Cancer Res, 74, 1105-1115 (2014). Moreover, SRSF1 has been demonstrated to be a direct transcriptional target of the oncogene c-Myc further cementing the role of SRSF1 in oncogenesis. Das et al., Cell reports, 1, 110-117 (2012).

In this example, the inventors demonstrated that SRSF1 is capable of regulating the stress-induced alternative splicing of the oncogene MDM2. Indeed, they show that pediatric rhabdomyosarcoma tumors spontaneously expressing MDM2-ALT1 also show elevated levels of SRSF1 compared to matched normal muscle tissue (FIG. 8). This is important because MDM2-ALT1, the alternative splice variant of MDM2 that is predominantly generated in response to DNA damage, is also strongly associated with several cancer types. In vitro studies have demonstrated the tumorigenic potential of MDM2-ALT1. Steinman et al., J Biol Chem, 279, 4877-4886 (2004). In vivo, the mouse homolog Mdm2-b has been shown to lead to tumorigenesis in a syngeneic mouse model while an MDM2-ALT1 like protein-accelerated lymphomagenesis in Eμ-Myc mice. Fridman et al., Cancer Res, 63, 5703-5706 (2003) Paradoxically, MDM2-ALT1 expression results in the upregulation of the tumor-suppressor p53 and the activation of a subset of its transcriptional targets. This is because MDM2-ALT1 lacks the p53-binding domain and is therefore incapable of binding and negatively regulating p53. Moreover, it functions as a dominant negative protein by dimerizing with (via the RING domain) and sequestering full-length MDM2. Zheng et al., Nature communications, 4, 2996 (2013). Interestingly, a recent study demonstrated that in the context of tumors presenting with mutant gain-of-function p53, the expression of MDM2-ALT1 can inhibit the degradation of mut-p53 by interfering with the function of full-length MDM2 leading to accumulation of mutant p53 in tumor cells. However, several tumor types including rhabdomyosarcomas that present with MDM2-ALT1 have predominantly wild-type p53. Kraus et al., Int J Cancer, 80, 930-934 (1999). This indicates that perhaps some effects of MDM2 alternative splicing are p53-independent. It is therefore unclear whether MDM2-ALT1 is capable of promoting transformation through other p53 family members such as p63 and p73 or other pathways entirely.

Opportunity for therapeutic intervention: Because the chief function of full-length MDM2 is to promote the degradation of p53, modulating the splicing of MDM2 to yield splice variants incapable of such regulation, could prove to be a valuable strategy to manipulate p53 levels. For example, in tumors presenting with mutant p53 and MDM2-ALT1, blocking the SRSF1 binding site would facilitate the expression of more full-length transcripts and consequently, more functional full-length MDM2 protein to degrade mut-p53. The inventors show that treatment with antisense oligonucleotides to block the SRSF1 binding site in MDM2 exon 11 promotes a decrease in the MDM2-ALT1 alternatively spliced transcript even under stress. These results demonstrate the efficacy of the use of antisense oligonucleotides for targeting this site for splicing modulation of MDM2.

Importantly, it is likely that there are positive elements that antagonize the regulation of SRSF1 in MDM2 exon 11. Once these are identified, they could similarly be targeted to generate more MDM2-ALT1 and reactivate wild-type p53 (MDM2-ALT1 stabilizes p53 when by opposing full-length MDM2, thus inducing massive apoptosis to combat the action of other constitutively-active oncogenes. In short, controlling the ratio of the MDM2 splice isoforms using antisense oligonucleotides is an attractive strategy to control p53 levels, whether wild-type or mutant in cancer cells.

The inventors have provided evidence that overexpression and increased binding of SRSF1 to MDM2 exon 11 are sufficient to drive the expression MDM2-ALT1. This is first description of a molecular mechanism underpinning the alternative splicing of MDM2 under damage, raising the possibility that persistent MDM2-ALT1 splicing observed in cancers is regulated by the same means. By understanding the molecular mechanisms regulating MDM2 splicing in response to damage and potentially in cancer, they have further identified novel splice modulation strategies for adjusting MDM2 levels in cancers with elevated MDM2-ALT1 and SRSF1 expression. Future studies to identify other modifiers of MDM2 splicing will enable a comprehensive understanding of stress and cancer induced splicing and the design of specific splicing modulation strategies.

Example 2

Splicing Factor SRSF2 Rescues Skipping of Endogenous MDM2 Under Damage

MDM2 gene amplification is observed in approximately 7% of all human malignancies, with the highest percentage in soft-tissue sarcomas (20%), osteosarcomas (16%), and esophageal carcinomas (13%). One of the ways in which the levels of MDM2 transcripts are regulated is through its alternative splicing under conditions of genotoxic stress. By excluding exons containing its p53 binding domain, alternatively-spliced transcripts of MDM2 exert tumor protective activity by upregulating p53. One of these transcripts, MDM2-ALT1, is comprised of exons 3 and 12 and is the most commonly observed isoform in response to stress. The inventors hypothesis is that there are cis elements and trans factors that are responsible for mediating the alternative splicing of MDM2 and these sites can be targeted to activate p53.

In order to study the alternative splicing of MDM2, a damage-inducible minigene system was developed. The MDM2 3-11-12s minigene recapitulates the splicing of the endogenous gene by excluding its intervening exon under genotoxic stress. Using a SELEX-based bioinformatics prediction algorithms in ESEfinder 3.0 we identified conserved consensus sequences for splicing regulator SRSF2 in exon 11 of MDM2.

FIG. 9 shows the results of experiments carried out to demonstrate that splicing factor SRSF2 promotes generation of the MDM2-FL transcript, as described in the figure legend provided herein.

Figure 10A:
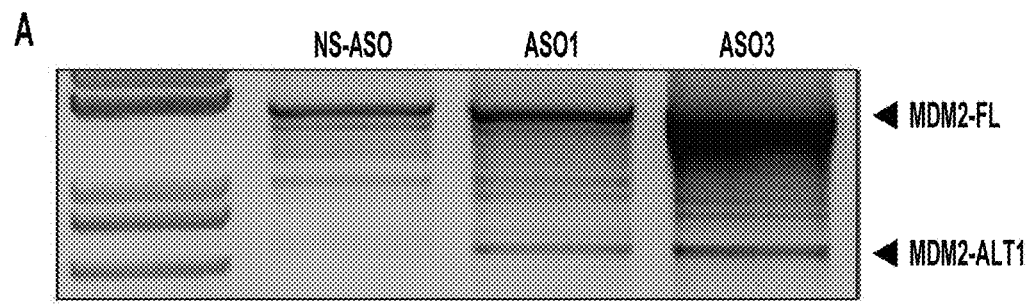
FIGS. 10A and 10B provide images and a graph showing ASOs targeting SRSF2 sites in MDM2 exon 11. (A) shows ASOs targeting SRSF2 sites in MDM2 exon 11 (ASO1, ASO3) have been successful in modulating the alternative splicing of MDM2 toward MDM2-ALT1 in SMS-CTR cells at 1000 pmol doses after 24 hours by nucleofection as compared to the non-specific (NS-ASO) control, while (B) shows nucleofection of 1000 pmol of ASOs targeting SRSF2 sites in MDM2 exon 11 (ASO1, ASO3) has been successful in modulating the cell cycle progression of SMS-CTR cells, with an increase of cells in G2/M arrest after 24 hours as compared to the non-specific (NS-ASO) control.
Figure 10B:
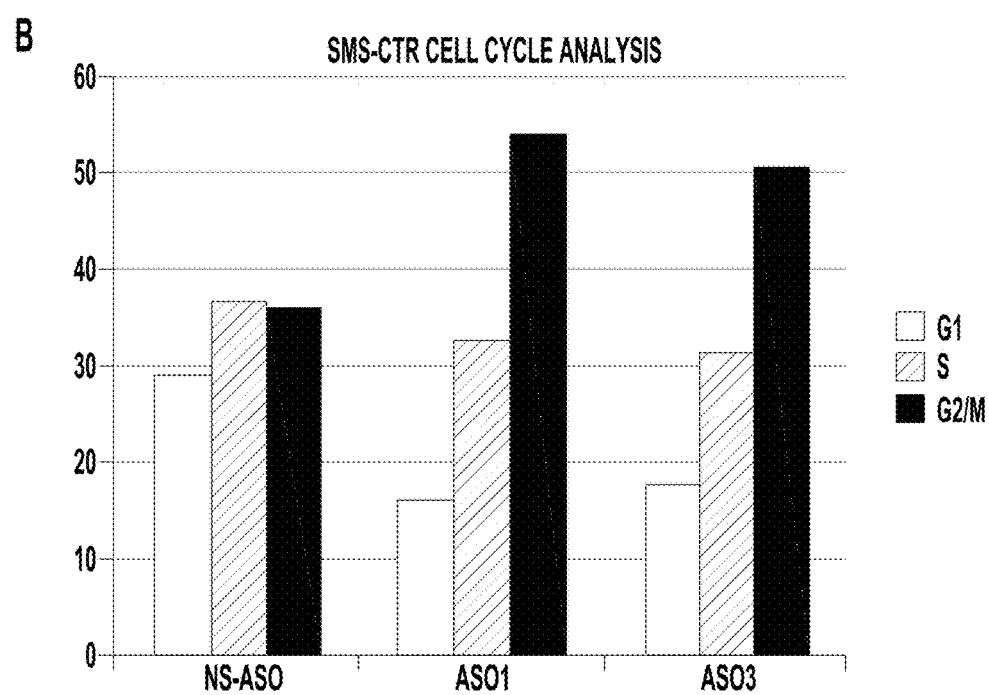

The inventors have shown that SRSF2 promotes the inclusion of exon 11 under damage both in vitro and in vivo using our MDM2 minigene. The binding data has demonstrated that upon mutation, binding of SRSF2 is attenuated. Also, overexpression of SRSF2 promotes the inclusion of MDM2 exon 11 under damage, whereas knockdown induces the skipping of MDM2. Importantly, antisense oligonucleotides (ASOs) targeting SRSF2 binding sites push endogenous MDM2 splicing toward MDM2-ALT1. In summary, a critical regulator of MDM2 alternative splicing has been identified. By titrating the amount of MDM2-ALT1 endogenously, ASOs can be utilized as a strategy for anticancer therapy wherein MDM2 amplification and wild-type p53 is observed. See FIGS. 10A and 10B.

Example 3

Antisense Oligonucleotides Against SFSF2 Sites in Exon 11 Induce Expression of MDM2-ALT1

Figure 11:
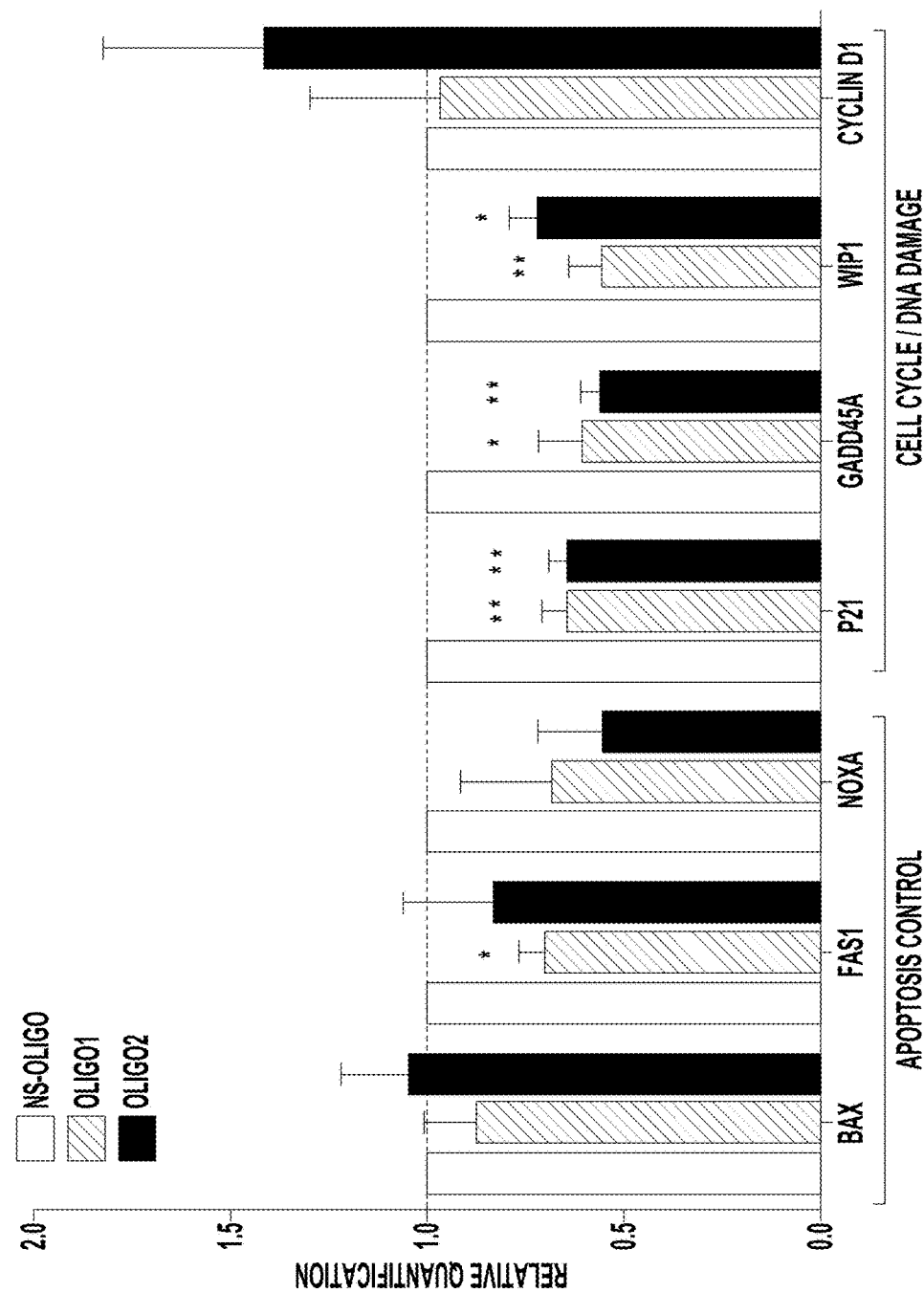
FIG. 11 provides a graph showing oligonucleotides encompassing SRSF1 binding sites in MDM2 exon 11 reduce the expression of genes involved in apotosis and cell cycle. 500 nM oligonucleotide were transfected into MCF7 cells as described in Comiskey et al. RNA was extracted and subjected to a qRT-PCR assay for the genes indicated FIGS. 12A-12C provide a scheme and graphs showing Antisense oligonucleotides (ASOs) targeting SRSF2 sites in MDM2 exon 11 induces expression of MDM2-ALT1. A. Schematic of binding site for ASOs targeting SRSF2 sites in MDM2 exon 11. B. MCF7 cells or SMS-CTR cells were transfected with non-specific (NS-ASO) or SRSF2 site-specific ASOs (ASO1, ASO3, ASO12) for 24 hours and subjected to qRT-PCR for MDM2-ALT1 and normalized to GAPDH. ASO1, ASO2, and ASO3 induced expression of MDM2-ALT1 as compared to NS-ASO in MCF7 cells (n=4, p=0.0277 ASO1, p=0.0055 ASO3, p=0.0143 ASO3) and SMS-CTR cells (n=3, p=0.0172 ASO1, p=0.0110 ASO3). F. Cell cycle analysis of MCF7 transfected with non-specific (NS-ASO) or SRSF2 site-specific ASOs (ASO1, ASO2, ASO3). Cells were transfected for 24 hours, then fixed and stained with propidium iodide, and analyzed by flow cytometry. SRSF2-specific ASOs increased the percentage of cells in G1 arrest as compared to NS-ASO.

To test whether treatment of oligonucleotides encompassing SRSF1 sites in MDM2 exon 11 modulated the p53 pathway we designed qPCR primers against transcriptional targets of p53. We used cDNA collected from MCF7 cells treated with 500 nM oligonucleotide for 24 hours that showed modulation of MDM2-ALT1 expression (FIG. 11) and looked at the level of mRNA expression of p53 pathway members. We report that both oligonucleotides significantly downregulated the expression of p21, GADD45A, and WIP1 as compared to the non-specific oligonucleotide control. These data indicate that the not only does treatment of SRSF1 oligonucleotides attenuate the expression of MDM2-ALT1, but also has a function impact on p53 targets. Therefore, treatment of these oligonucleotides could be of therapeutic benefit in cancers presenting with gain-of-function (GOF) p53 mutations by turning off p53's transcriptional program through degradation by full-length MDM2.

SSO treatment and cell cycle targets—2'O-methyl SSOs were generated from Trilink. SSOs specific to MDM2 exon 11 (OLIGO1: 'CUAUCAGGCAGGGGAGAGUG', OLIGO2: 'CAGGCAGGGGAGAGUGAUAC') or a non-specific ASO 'AUAUAGCGACAGCAUCUUCC') were transfected in MCF7 cells with Lipofectamine 3000 (Catalog 15338-100) from Life Technologies (Carlsbad, Calif., USA) according to the manufacturer's protocol. Cells were harvested for RNA using an RNeasy kit from Qiagen and subjected to qRT-PCR using the following conditions: 50° C. 2', 95° C. 10', 40 cycles of 95° C. 15", 60° C. 1' on a 7900HT Fast-Real Time System.

Figure 12A:
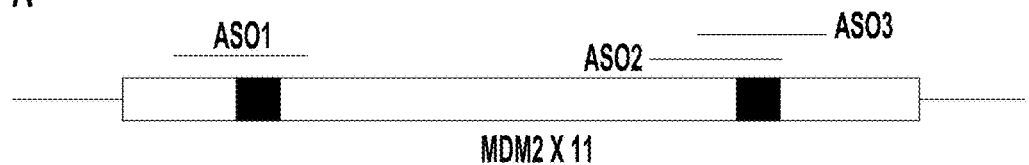

To test whether SRSF2 sites in exon 11 of MDM2 regulate the endogenous gene, we designed ASOs against each of our identified sites (FIG. 12A). These antisense oligonucleotides contain a 2'-O-methyl modified RNA base and a phosphorothioate sugar backbone, which provides additional stability to the RNA molecule. Yoo et al., Nucleic Acids Res 32(6): 2008-2016 (2004).

Figure 12B:
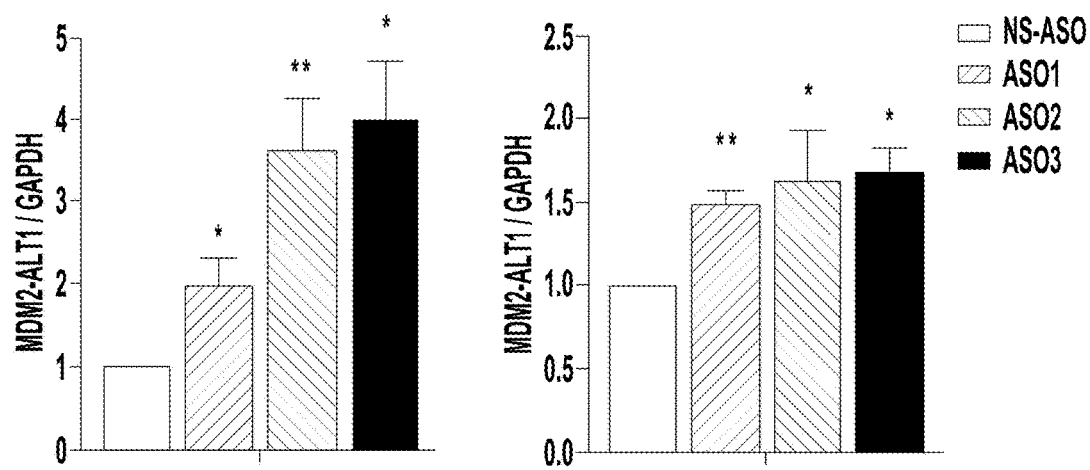
Figure 12C:
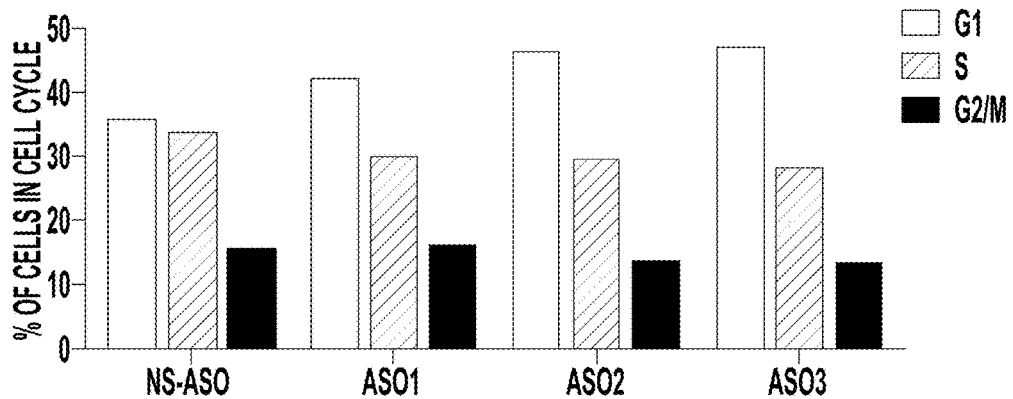

These ASOs were transfected into MCF7 and SMS-CTR cells, a rhabdomyosarcoma cell line. We then performed a qRT-PCR assay specific for MDM2-ALT1, which targets the splice junction between exons 3 and 12. We observed a statistically significant increase in expression of MDM2-ALT1 in both cell lines upon transfection of ASOs specific for SRSF2 binding sites in exon 11 (FIG. 12B). Increased expression of MDM2-ALT1 leads to the stabilization of the p53. Jeyaraj et al., Front Biosci (Landmark Ed) 14: 2647-2656 (2009). We previously showed that exogenous expression of MDM2-ALT1 leads to an increase in expression of genes involved in cell cycle arrest, as well as an increased proportion of cells in G1 arrest. Jacob et al., PLoS One 9(8): e104444 (2014). Thus, we next asked whether the increased expression of MDM2-ALT1 after ASO transfection would lead to a similar change in cell cycle progression. We transfected MCF7 cells with SRSF2 site-specific ASOs (FIG. 12A) for 24 hours then fixed and stained cells with propidium iodide for 24 hours then fixed and stained cells with propidium iodide. When we analyzed cells by flow cytometry we observed a significant increase in the proportion of cells in G1 arrest, as well as a decrease in cells undergoing division (FIG. 12C). These data suggest that these ASOs may be effective in promoting cell cycle arrest in cancer cells by inducing MDM2-ALT1 expression.

ASO treatment and cell cycle analysis—2'O-methyl ASOs were generated from Trilink. ASOs specific to MDM2 exon 11 (#1 'CUGCCUGAUACACAGUAACU', #2 'UUUCAGCAUCUUCUUCAAAU', #3 'GAAAUUUCAGGAUCUUCUUC') or a non-specific ASO ('AUAUAGCGACAGCAUCUUCC') were transfected in MCF7 cells with Lipofectamine 3000 (Catalog 15338-100) from Life Technologies (Carlsbad, Calif., USA) according to the manufacturer's protocol. For transfection of ASOs, 1.5 million SMS-CTR cells were nucleofected using Nucleofector Kit R (Cotolog Number VACA-1001) using program X-001 on an Amaxa Nucleofector II device. Cells were harvested for RNA using an RNeasy kit from Qiagen and subjected to RT-PCR using conditions described above. Cells were fixed in 75% ethanol for 24 hours at 4° C. Cells were then spun down 5000 rpm for 5 minutes. Ethanol was aspirated, and cells were stained in 500 µl cell staining solution (100 U/mL RNase A, 0.05 mg/mL propidium iodide, 1 mg/mL L-dextrose in PBS) in dark at room temperature for 30 minutes. Cells were strained through a 40 nm strainer and analyzed on a BD flow LSRII cytometer running FACSDiva software.

In order to determine whether other intervening exons between 3 and 11 were damage-responsive we cloned exons 4-10 individually into the damage-responsive MDM2 3-11-12s minigene. We report that only the MDM2 3-4-12s minigene is capable of damage-inducible alternative splicing (FIG. 13B) in response to UVC and cisplatinum stress. None of the remaining minigenes (3-5-12s, 3-6-12s, 3-7-12s, 3-8-12s, 3-9-12s or 3-10-12s) show induced exon skipping in response to damage treatment. Furthermore, this exon contains predicted binding sites for splicing regulators SRSF1 and SRSF2, most of which are conserved between mouse and human MDM2 (FIG. 13A). We report that these sites, especially for SRSF2, have a high predicted affinity for SRSF1 and SRSF2, respectively (FIG. 13C). We hypothesize that these sites could be targeted to control the splicing patterns of MDM2 just like the characterized sites in exon 11.

Minigene Transfection—MCF7 cells were seeded to 60% confluency and transfected with Lipofectamine 3000 (Catalog 15338-100) from Life Technologies (Carlsbad, Calif., USA) according to the manufacturer's protocol. For damage treatment, cells were split into treatment groups (normal, UV, or cisplatinum) under normal conditions, or 50 J/m$^2$ ultra-violet (UVC) or 75 µM cisplatinum for 24 h, then harvested for RNA using an RNeasy kit (Catalog 74106)

from Qiagen (Valencia, Calif., USA) and subjected to RT-PCR using conditions described in Comiskey et al. Comiskey et al., Nucleic Acids Res 43(8): 4202-4218 (2015).

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating cancer in a subject in need thereof, comprising administering a therapeutically effective amount of an antisense oligonucleotide that inhibits the binding of splicing regulator SRSF1 or SRSF2 to MDM2 exon 11, wherein the antisense oligonucleotide includes from 10 to 30 nucleotides, and a portion of the antisense oligonucleotide is complementary to the nucleotide sequence AGTTACTG or AGATCCTG, wherein the cancer exhibits elevated MDM2-ALT1 and SRSF1 expression.

2. The method of claim 1, wherein the splicing regulator is SRSF1.

3. The method of claim 2, wherein the oligonucleotide is a sense oligonucleotide, and a portion of the sense oligonucleotide comprises the nucleotide sequence GGCAGGGGA.

4. The method of claim 2, wherein the oligonucleotide is SEQ ID NO: 6 or SEQ ID NO: 7.

5. The method of claim 2, wherein the cancer comprises mutant tumor suppressor protein p53.

6. The method of claim 1, wherein the splicing regulator is SRSF2.

7. The method of claim 6, wherein the cancer comprises a wild-type form of tumor suppressor protein p53.

8. The method of claim 6, wherein the oligonucleotide is SEQ ID NO: 3, SEQ ID NO: 4, or SEQ ID NO: 5.

9. The method of claim 1, wherein the oligonucleotide is a siRNA.

10. The method of claim 1, wherein the oligonucleotide is a 2'-O-alkyl antisense oligonucleotide.

11. The method of claim 1, wherein the subject is also undergoing one or more cancer therapies selected from the group consisting of surgery, chemotherapy, radiotherapy, thermotherapy, immunotherapy, hormone therapy, or laser therapy.

* * * * *

UNITED STATES PATENT AND TRADEMARK OFFICE
CERTIFICATE OF CORRECTION

PATENT NO. : 10,465,193 B2
APPLICATION NO. : 15/594054
DATED : November 5, 2019
INVENTOR(S) : Dawn Suzan Chandler et al.

It is certified that error appears in the above-identified patent and that said Letters Patent is hereby corrected as shown below:

In the Specification

Column 1, Lines 15-18, under the heading Government Funding please delete the paragraph:
"This invention was made with Government support under grant number R01CA1335710 awarded by the National Institutes of Health and the National Cancer Institute. The Government has certain rights in the invention."

And replace it with:
--This invention was made with government support under Grant No. CA133571 from The National Institutes of Health. The government has certain rights in the invention.--

Signed and Sealed this
Third Day of January, 2023

Katherine Kelly Vidal
Director of the United States Patent and Trademark Office

```
                           SEQUENCE LISTING

<160> NUMBER OF SEQ ID NOS: 28

<210> SEQ ID NO 1
<211> LENGTH: 78
<212> TYPE: DNA
<213> ORGANISM: Homo sapiens

<400> SEQUENCE: 1
gtatatcaag ttactgtgta tcaggcaggg gagagtgata cagattcatt tgaagaagat      60
cctgaaattt ccttagct                                                   78

<210> SEQ ID NO 2
<211> LENGTH: 19
<212> TYPE: DNA
<213> ORGANISM: Homo sapiens

<400> SEQUENCE: 2
tatcaggcag gggagagtg                                                  19

<210> SEQ ID NO 3
<211> LENGTH: 20
<212> TYPE: RNA
<213> ORGANISM: Artificial Sequence
<220> FEATURE:
<223> OTHER INFORMATION: ASO1

<400> SEQUENCE: 3
cugccugaua cacaguaacu                                                 20

<210> SEQ ID NO 4
<211> LENGTH: 20
<212> TYPE: RNA
<213> ORGANISM: Artificial Sequence
<220> FEATURE:
<223> OTHER INFORMATION: ASO2

<400> SEQUENCE: 4
uccccugccu gauacacagu                                                 20

<210> SEQ ID NO 5
<211> LENGTH: 20
<212> TYPE: RNA
<213> ORGANISM: Artificial Sequence
<220> FEATURE:
<223> OTHER INFORMATION: ASO3

<400> SEQUENCE: 5
uuucaggauc uucuucaaau                                                 20

<210> SEQ ID NO 6
<211> LENGTH: 20
<212> TYPE: RNA
<213> ORGANISM: Artificial Sequence
<220> FEATURE:
<223> OTHER INFORMATION: ASO4

<400> SEQUENCE: 6
guaucaggca ggggagagug                                                 20
```

```
<210> SEQ ID NO 7
<211> LENGTH: 20
<212> TYPE: RNA
<213> ORGANISM: Artificial Sequence
<220> FEATURE:
<223> OTHER INFORMATION: ASO5

<400> SEQUENCE: 7
caggcagggg agagugauac                                                    20

<210> SEQ ID NO 8
<211> LENGTH: 32
<212> TYPE: DNA
<213> ORGANISM: Artificial Sequence
<220> FEATURE:
<223> OTHER INFORMATION: primer sequence

<400> SEQUENCE: 8
tcgaattcgc tagcattcct gtgactgagc ag                                      32

<210> SEQ ID NO 9
<211> LENGTH: 26
<212> TYPE: DNA
<213> ORGANISM: Artificial Sequence
<220> FEATURE:
<223> OTHER INFORMATION: primer sequence

<400> SEQUENCE: 9
taactcgagc ctcaacacat gactct                                             26

<210> SEQ ID NO 10
<211> LENGTH: 29
<212> TYPE: DNA
<213> ORGANISM: Artificial Sequence
<220> FEATURE:
<223> OTHER INFORMATION: primer sequence

<400> SEQUENCE: 10
gcctgcagct gattgaagga aatagggcg                                          29

<210> SEQ ID NO 11
<211> LENGTH: 26
<212> TYPE: DNA
<213> ORGANISM: Artificial Sequence
<220> FEATURE:
<223> OTHER INFORMATION: primer sequence

<400> SEQUENCE: 11
agggaattcg aagctagata tagtct                                             26

<210> SEQ ID NO 12
<211> LENGTH: 32
<212> TYPE: DNA
<213> ORGANISM: Artificial Sequence
<220> FEATURE:
<223> OTHER INFORMATION: primer sequence

<400> SEQUENCE: 12
gcggatcccc acctcacaga ttccagcttc gg                                      32

<210> SEQ ID NO 13
<211> LENGTH: 28
<212> TYPE: DNA
<213> ORGANISM: Artificial Sequence
<220> FEATURE:
```

```
<223> OTHER INFORMATION: primer sequence

<400> SEQUENCE: 13
ctgcagcaaa aatactaacc agggtctc                                          28

<210> SEQ ID NO 14
<211> LENGTH: 25
<212> TYPE: DNA
<213> ORGANISM: Artificial Sequence
<220> FEATURE:
<223> OTHER INFORMATION: primer sequence

<400> SEQUENCE: 14
cactggtgtc gtggagtttg tacgg                                             25

<210> SEQ ID NO 15
<211> LENGTH: 21
<212> TYPE: DNA
<213> ORGANISM: Artificial Sequence
<220> FEATURE:
<223> OTHER INFORMATION: primer sequence

<400> SEQUENCE: 15
gggcaggaat ccactcctat g                                                 21

<210> SEQ ID NO 16
<211> LENGTH: 21
<212> TYPE: RNA
<213> ORGANISM: Artificial Sequence
<220> FEATURE:
<223> OTHER INFORMATION: RNA probe

<400> SEQUENCE: 16
uaucaggcag gggagaguga u                                                 21

<210> SEQ ID NO 17
<211> LENGTH: 21
<212> TYPE: RNA
<213> ORGANISM: Artificial Sequence
<220> FEATURE:
<223> OTHER INFORMATION: RNA probe

<400> SEQUENCE: 17
uaucagaaag gggagaguga u                                                 21

<210> SEQ ID NO 18
<211> LENGTH: 75
<212> TYPE: DNA
<213> ORGANISM: Artificial Sequence
<220> FEATURE:
<223> OTHER INFORMATION: primer sequence

<400> SEQUENCE: 18
agtaatacga ctcactatag ggattacaag gatgacgacg ataagagccc gggcggatcc        60
ccacctcaca gattc                                                        75

<210> SEQ ID NO 19
<211> LENGTH: 33
<212> TYPE: DNA
<213> ORGANISM: Artificial Sequence
<220> FEATURE:
<223> OTHER INFORMATION: primer sequence

<400> SEQUENCE: 19
acttacggcc caacatctgt tgcaatgtga tgg                                    33
```

<210> SEQ ID NO 20
<211> LENGTH: 69
<212> TYPE: DNA
<213> ORGANISM: Artificial Sequence
<220> FEATURE:
<223> OTHER INFORMATION: primer sequence

<400> SEQUENCE: 20
agtaatacga ctcactatag ggattacaag gatgacgacg ataaggttgg ctctgactgt    60
accaccatc                                                            69

<210> SEQ ID NO 21
<211> LENGTH: 33
<212> TYPE: DNA
<213> ORGANISM: Artificial Sequence
<220> FEATURE:
<223> OTHER INFORMATION: primer sequence

<400> SEQUENCE: 21
acttacggct gaagggtgaa atattctcca tcc                                 33

<210> SEQ ID NO 22
<211> LENGTH: 21
<212> TYPE: RNA
<213> ORGANISM: Artificial Sequence
<220> FEATURE:
<223> OTHER INFORMATION: SRSF1-WT

<400> SEQUENCE: 22
uaucaggcag gggagaguga u                                              21

<210> SEQ ID NO 23
<211> LENGTH: 21
<212> TYPE: RNA
<213> ORGANISM: Artificial Sequence
<220> FEATURE:
<223> OTHER INFORMATION: SRSF1-MUT

<400> SEQUENCE: 23
uaucagaaag gggagaguga u                                              21

<210> SEQ ID NO 24
<211> LENGTH: 20
<212> TYPE: RNA
<213> ORGANISM: Artificial Sequence
<220> FEATURE:
<223> OTHER INFORMATION: SRSF1 3'UTR-siRNA sense

<400> SEQUENCE: 24
uuggcaguau ugaccuuauu                                                20

<210> SEQ ID NO 25
<211> LENGTH: 19
<212> TYPE: RNA
<213> ORGANISM: Artificial Sequence
<220> FEATURE:
<223> OTHER INFORMATION: SRSF1 3'UTR-siRNA antisense

<400> SEQUENCE: 25
uaggucaaua cugccaauu                                                 19

<210> SEQ ID NO 26
<211> LENGTH: 21
<212> TYPE: RNA

```
<213> ORGANISM: Artificial Sequence
<220> FEATURE:
<223> OTHER INFORMATION: CTRL sense

<400> SEQUENCE: 26
aagguccggc uccccaaau g                                          21

<210> SEQ ID NO 27
<211> LENGTH: 21
<212> TYPE: RNA
<213> ORGANISM: Artificial Sequence
<220> FEATURE:
<223> OTHER INFORMATION: CTRL antisense

<400> SEQUENCE: 27
cauuuggggg agccggaccu u                                         21

<210> SEQ ID NO 28
<211> LENGTH: 20
<212> TYPE: RNA
<213> ORGANISM: Artificial Sequence
<220> FEATURE:
<223> OTHER INFORMATION: non-specific ASO

<400> SEQUENCE: 28
auauagcgac agcaucuucc                                           20
```